US010426976B1

(12) United States Patent
Parsai et al.

(10) Patent No.: US 10,426,976 B1
(45) Date of Patent: Oct. 1, 2019

(54) NITINOL ORGAN POSITIONER TO PREVENT DAMAGE TO HEALTHY TISSUE DURING RADIATION ONCOLOGY TREATMENTS

(71) Applicant: The University of Toledo, Toledo, OH (US)

(72) Inventors: E. Ishmael Parsai, Toledo, OH (US); Mohammad Elahinia, Toledo, OH (US)

(73) Assignee: The University of Toledo, Toledo, OH (US)

( * ) Notice: Subject to any disclaimer, the term of this patent is extended or adjusted under 35 U.S.C. 154(b) by 275 days.

(21) Appl. No.: 15/630,606

(22) Filed: Jun. 22, 2017

Related U.S. Application Data

(60) Provisional application No. 62/353,347, filed on Jun. 22, 2016.

(51) Int. Cl.
 *A61N 5/01* (2006.01)
 *A61N 5/10* (2006.01)

(52) U.S. Cl.
 CPC ......... *A61N 5/1069* (2013.01); *A61N 5/1049* (2013.01); *A61N 5/1077* (2013.01)

(58) Field of Classification Search
 CPC ...... A61M 29/02; A61M 25/04; A61M 25/10; A61M 2210/1085; A61M 25/0017; A61M 2202/0496; A61M 2205/0266; A61M 25/0074; A61M 25/0155; A61M 25/1011; A61M 27/008; A61M 2025/0213; A61M 2205/50; A61M 25/0026; A61M 2025/105; A61M 25/1018; A61M 25/10181; A61M 25/10184; A61M 25/1036; A61M 25/1038
See application file for complete search history.

(56) References Cited

U.S. PATENT DOCUMENTS

| | | | |
|---|---|---|---|
| 4,601,283 A | | 7/1986 | Chikama |
| 5,653,683 A | * | 8/1997 | D'Andrea ............ A61N 5/1014 600/2 |
| 6,068,621 A | | 5/2000 | Balceta et al. |
| 6,390,968 B1 | | 5/2002 | Harmon |
| 6,402,677 B1 | | 6/2002 | Jacobs |
| 6,699,171 B2 | | 3/2004 | Harmon |
| 6,746,465 B2 | | 6/2004 | Diederich et al. |
| 8,532,791 B2 | | 9/2013 | Wanna |

(Continued)

FOREIGN PATENT DOCUMENTS

| | | |
|---|---|---|
| CN | 1803348 A | 7/2006 |
| CN | 102703844 A | 10/2012 |

(Continued)

OTHER PUBLICATIONS

Andani et al.,"Modeling and Simulation of SMA Medical Devices Undergoing Complex Thermo-mechanical Loadings", Journal of Materials Engineering and Performance, May 28, 2014, Abstract.

(Continued)

*Primary Examiner* — Thaddeus B Cox
*Assistant Examiner* — Joshua Daryl D Lannu
(74) *Attorney, Agent, or Firm* — MacMillan, Sobanski & Todd, LLC

(57) ABSTRACT

Devices, systems, and methods for repositioning organs, such as the rectum, during radiation therapy treatments, are described.

10 Claims, 33 Drawing Sheets
(33 of 33 Drawing Sheet(s) Filed in Color)

(56) References Cited

U.S. PATENT DOCUMENTS

| | | | |
|---|---|---|---|
| 8,961,383 | B2 | 2/2015 | Parsai et al. |
| 2003/0032851 | A1 | 2/2003 | Apple et al. |
| 2004/0147811 | A1 | 7/2004 | Diederich et al. |
| 2005/0080313 | A1 | 4/2005 | Stewart et al. |
| 2006/0014997 | A1 | 1/2006 | Kindlein et al. |
| 2006/0020156 | A1 | 1/2006 | Shukla |
| 2006/0100475 | A1* | 5/2006 | White .................. A61N 5/1015 600/3 |
| 2006/0116546 | A1 | 6/2006 | Eng |
| 2007/0106108 | A1 | 5/2007 | Hermann et al. |
| 2009/0112248 | A1 | 4/2009 | Maloney |
| 2012/0018413 | A1 | 1/2012 | Pilch et al. |
| 2015/0360288 | A1 | 12/2015 | Zalewski |
| 2016/0107393 | A1 | 4/2016 | Hartmann et al. |
| 2016/0279388 | A1* | 9/2016 | Barrish ............. A61M 25/0155 |
| 2017/0014169 | A1 | 1/2017 | Dean et al. |

FOREIGN PATENT DOCUMENTS

| | | |
|---|---|---|
| CN | 102766833 A | 11/2012 |
| EP | 1402922 A1 | 3/2004 |
| EP | 1618924 A1 | 1/2006 |
| EP | 2989514 A1 | 3/2016 |
| WO | 2008124149 A1 | 10/2008 |
| WO | 2010127646 A2 | 11/2010 |

OTHER PUBLICATIONS

Bormann, et al., "Tailoring Selective Laser Melting Process Parameters for NiTi Implants", Journal of Materials Engineering and Performance, vol. 21 (12) December, pp. 2012-2519.

Bormann, Structure and thermomechanics of selective laser melted nickel-titanium, pp. 1-71.

Greiner, et al., "High strength, low stiffness, porous NiTi with superelastic properties", Acta Biomaterialia 1 (2005) pp. 705-716.

Haberland, et al., "Additive Manufacturing of Shape Memory Devices and Pseudoelastic Components", The American Society of Mechanical Engineering, 2013, Abstract.

Jahadakbar, et al., "Finite Element Simulation and Additive Manufacturing of Stiffness-Matched NiTi Fixation Hardware for Mandibular Reconstruction Surgery", Bioengineering 2016, 3, 36, pp. 1-20.

Kruth, "Consolidation phenomena in laser and powder-bed based layered manufacturing", Elsevier, Annals of the CIRP vol. 56/2/ 2007, pp. 730-759.

Ma, et al., "Advanced Processing Techniques: Additive, Porous, and Others", ICOMAT, 2017, Abstract.

Narayanan, et al., "Control of a shape memory alloy-actuated rotary manipulator using an artificial neural network-based self-sensing technique", Journal of Intelligent Material Systems and Structures, 2016, pp. 1-10.

Parsai, et al., "An Innovative Critical Organ Repositioner Device for Use During Radiotherapy Treatments", Medical Physics, 2014, Abstract.

Saedi, et al., "Additive Manufacturing: Building the Pathway Towards Process and Material Qualification", TMS, 2016, Abstract.

Yadroitsev, et al., "Surface Morphology in Selective Laser Melting of Metal Powders", Science Direct, Physics Procedia 12 (2011) 264-270.

EP Communication, Extended Search Report, Application No. 08754074.6-1659, dated Oct. 31, 2014.

EP Communication Pursuant to Article 94(3) EPC, Application No. 08754074.6-1115, dated Oct. 15, 2018.

EP Communication Pursuant to Article 94(3) EPC, Application No. 08754074.6-1115, dated Jul. 17, 2018.

PCT International Search Report, referring to Dean et al., 2017/ 0014169, published Jan. 9, 2017, Application No. PCT/US15/ 20043, dated Jul. 28, 2015.

PCT International Search Report and Written Opinion, referring to Parsai et al., Pub. No. WO2008/124149, PCT/US08/04550, dated Jul. 25, 2008.

PCT International Preliminary Report on Patentability, referring to Parsai et al., Pub. No. 2008/124149, PCT/US08/04550, dated Oct. 13, 2009.

* cited by examiner

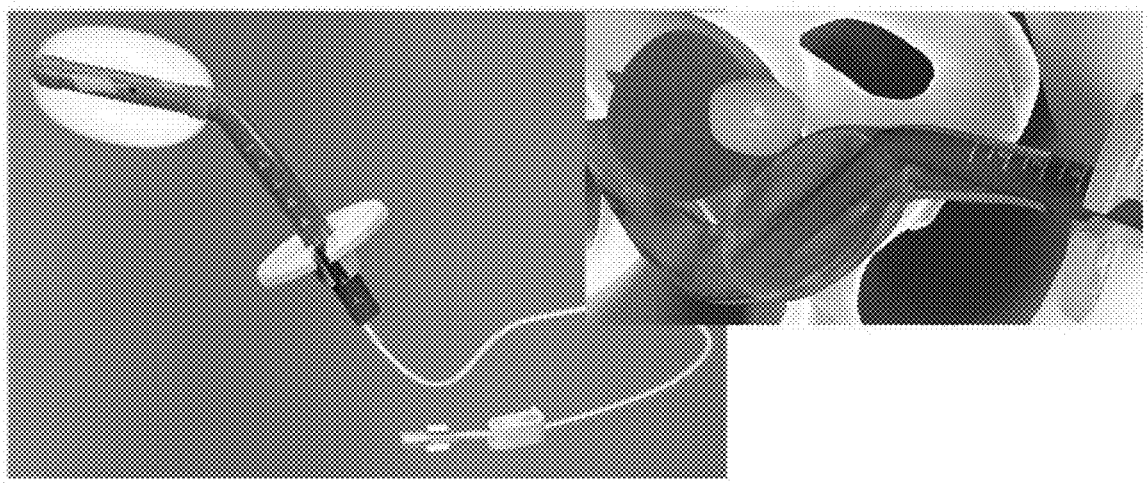
PRIOR ART FIG. 7A

Table 1. Parameters describing SMA-actuated rotary manipulator.

| Parameters | Value | Unit |
|---|---|---|
| SMA wire's mass per unit length | $1.14e^{-4}$ | kg/m |
| SMA wire's cross-sectional area | $4.71e^{-4}$ | $m^2$ |
| Initial length of SMA wire | 0.90 | M |
| SMA wire's initial strain | 0.04 | |
| SMA wire's initial stress | 150.00 | MPa |
| Ambient temperature | 20.00 | °C |
| SMA wire's initial martensite fraction | 1.00 | |
| Austenite start temperature | 68.00 | °C |
| Austenite final temperature | 78.00 | °C |
| Martensite start temperature | 52.00 | °C |
| Martensite final temperature | 42.00 | °C |
| Payload mass | 57.19 | G |
| Moving link mass | 19.70 | G |
| Bias spring stiffness | 3.87 | N/m |
| Maximum resistance | 57.25 | Ω |
| Minimum resistance | 47.50 | Ω |

SMA: shape memory alloy.

FIG. 10

NITINOL ORGAN POSITIONER TO PREVENT DAMAGE TO HEALTHY TISSUE DURING RADIATION ONCOLOGY TREATMENTS

RELATED APPLICATIONS

This application claims priority to U.S. Provisional Application No. 62/353,347 filed under 35 U.S.C. § 111(b) on Jun. 22, 2016, the disclosure of which is incorporated herein by reference in its entirety.

STATEMENT REGARDING FEDERALLY SPONSORED RESEARCH

This invention was made with no government support. The government has no rights in this invention.

BACKGROUND OF THE INVENTION

During the course of radiation therapy, radiation-induced chronic morbidities may be observed in nearby critical structures. For younger patients and for patients with longer life expectancy, RT-induced second malignancies will likely increase. Curative doses of radiation in many instances may lead to good disease control but cause radiation-induced chronic morbidities in treatment areas. These include interstitial capillary injury of the myocardium leading to an increased incidence of coronary artery disease, cardiomyopathy, and pulmonary interstitial fibrosis, which could occur during lung or breast treatments. These toxicities are dose related, and reducing the radiation damage to nearby critical structures is highly desirable and very relevant to the patient's quality of life.

There is a large body of data in literature on tissue tolerances which shows it is important to respect the tolerance of critical structures such as the heart, lungs, esophagus, etc., and reduce associated morbidities while improving the quality of life. In most clinical situations, the radiation oncologist compromises the upper level of achieving specific tumoricidal dose to the tolerance doses of the nearby normal tissues. With the advent of Intensity-Modulated Radiation Therapy (IMRT) as a new radiation modality, some relief in sparing critical organs has been achieved as this technique has the potential to increase the therapeutic ratio. However, with newer treatments of stereotactic body radiotherapy (SBRT) for many disease sites, where in a smaller number of fractions a much larger dose per fraction is delivered, there are times when normal tissue located in the vicinity or path of the beam has to be sacrificed.

As an example, for cancers of the pelvis such as prostate cancer, the rectum is a key dose-limiting structure. Increased rectal dose can lead to acute proctitis, potential serious late toxicities, chronic irritation, bleeding, and ulceration. Currently, there is no easy or effective solution to place a distance between the rectum and the field of radiation. This is true for conventional EBRT, image-guided IMRT, and high dose rate (HDR) brachytherapy. Lowering dose to rectal tissue in newer modalities, such as SBRT with low fractionation and much higher dose per fraction, is of even greater importance. SBRT has rapidly gained acceptance in the radiation oncology community for a number of excellent incentives from the patient's point of view, including a non-invasive treatment, and a shorter treatment course compared to conventional EBRT. From the physician's perspective, SBRT of prostate offers cancer control rates equivalent to those of brachytherapy, conventional external beam IGRT, or surgery.

With HDR treatment of prostate, cervical, and endometrial cancer as well, where a strong radioactive source is often positioned to dwell in the vicinity of the rectum, displacing the anterior rectal wall even a short distance is highly desirable.

No minimally invasive device currently exists that relocates the rectum away from the field of radiation. A known method involves the injection of a biodegradable spacer between the prostate and the rectum. However, the biodegradable spacer is a gel that takes an average of 6 to 12 months to absorb after the injection. Furthermore, with current prostate fixation methods, such as a rectal balloon, the rectum wall anterior is still exposed to higher doses of radiation than desired.

It would be advantageous to discover devices, systems, and methods for repositioning critical structures, such as the rectum, during radiation therapy treatments.

SUMMARY OF THE INVENTION

Provided is an organ repositioner device that includes an inflatable balloon mounted on a bendable tube defining a lumen, the lumen housing an assembly of a shape memory (SM) element and a superelastic (SE) element. The SM element comprises a first shape memory alloy and has a first shape set form. The SE element comprises a second shape memory alloy and has a second shape set form. The bendable lumen bends upon shape transformations of the assembly. The assembly has an equilibrium shape between the first shape set form and the second shape set form. In some embodiments, the SM element is disposed around the SE element. In other embodiments, the SE element is disposed around the SM element. In certain embodiments, the organ repositioner device comprises a plurality of inflatable balloons mounted on the bendable tube.

In certain embodiments, upon cooling the organ repositioner device deforms toward the second shape set form, and heating drives the organ repositioner device toward the first shape set form. In certain embodiments, the SM element is a round wire and the SE element is a flat wire, where the round wire is wrapped around the flat wire. In certain embodiments, the SM element is a round wire and the SE element is a flat wire, where the flat wire is wrapped around the round wire. In certain embodiments, the first shape memory alloy comprises a NiTi alloy. In certain embodiments, the second shape memory alloy comprises a NiTi alloy. In certain embodiments, the first shape memory alloy and the second shape memory alloy are different NiTi alloys. In certain embodiments, the device further includes a controller in electrical communication with the SM element and the SE element, where the controller is configured to apply a voltage in the organ repositioner device.

Also provided is a method of administering a radiation therapy to a prostate, the method comprising using the organ repositioner device described herein to displace a rectum away from a prostate with respect to a radiation beam path, and then administering a radiation therapy to the prostate through the radiation beam path. In certain embodiments, the organ repositioner device comprises a controller that monitors electrical resistance in the organ repositioner device to determine an actuation state of the organ repositioner device.

Also provided is a method of repositioning an organ, the method comprising inserting an organ repositioner device into an anatomical location, where the organ repositioner device comprises an assembly of an SM element and an SE element, the SM element and the SE element comprising memory shape alloys, and actuating the assembly to cause the organ repositioner device to reposition an organ near the anatomical location. In certain embodiments, the actuation is caused by cooling the assembly. In certain embodiments, the actuation is caused by heating the assembly. In certain embodiments, the method further includes monitoring the actuation of the assembly by measuring electrical resistance in the assembly. In certain embodiments, the actuation is controlled using an artificial neural network. In certain embodiments, the method further includes administering a radiation therapy to or nearby the anatomical location.

Also provided is a method of repositioning an organ for a radiation treatment, the method comprising positioning an organ repositioner device in a first configuration in an anatomical location, cooling or heating the organ repositioner device to deform the organ repositioner into a second configuration, wherein deformation into the second configuration causes the organ repositioner device to reposition an organ at or near the anatomical location, and sensorlessly monitoring the deformation of the organ respositioner device by measuring electrical resistance in the organ repositioner. In certain embodiments, the method further comprises administering a radiation treatment to or nearby the anatomical location. In certain embodiments, the organ repositioner device comprises an assembly of two memory shape alloys. In particular embodiments, the assembly comprises a superelastic element and a shape memory element.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

PRIOR ART FIG. 7A: Conventional endorectal balloon (ERB) that can stabilize the rectum and the prostate during the radiation therapy of the prostate.

FIG. 10: Table 1, displaying parameters describing SMA-actuated rotary manipulator.

DETAILED DESCRIPTION OF THE INVENTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

In the treatment of prostate cancer using radiation therapy (RT), one persisting challenge is reducing radiation dose to critical surrounding structures such as the rectum while delivering an effective ablative dose to the target. Planning and delivery of RT for prostate cancer must always carefully account for rectal dose. The rectum serves as a key dose-limiting structure; increased rectal dose can lead to acute proctitis and potential serious late toxicities, including chronic irritation, bleeding, or ulceration. The increasing use of hypofractionated regimens for prostate radiotherapy, in which higher doses per fraction are delivered over a smaller total number of treatment sessions, makes achieving a lower rectal dose of even greater importance. This problem currently has no effective solution.

Figure 1A:
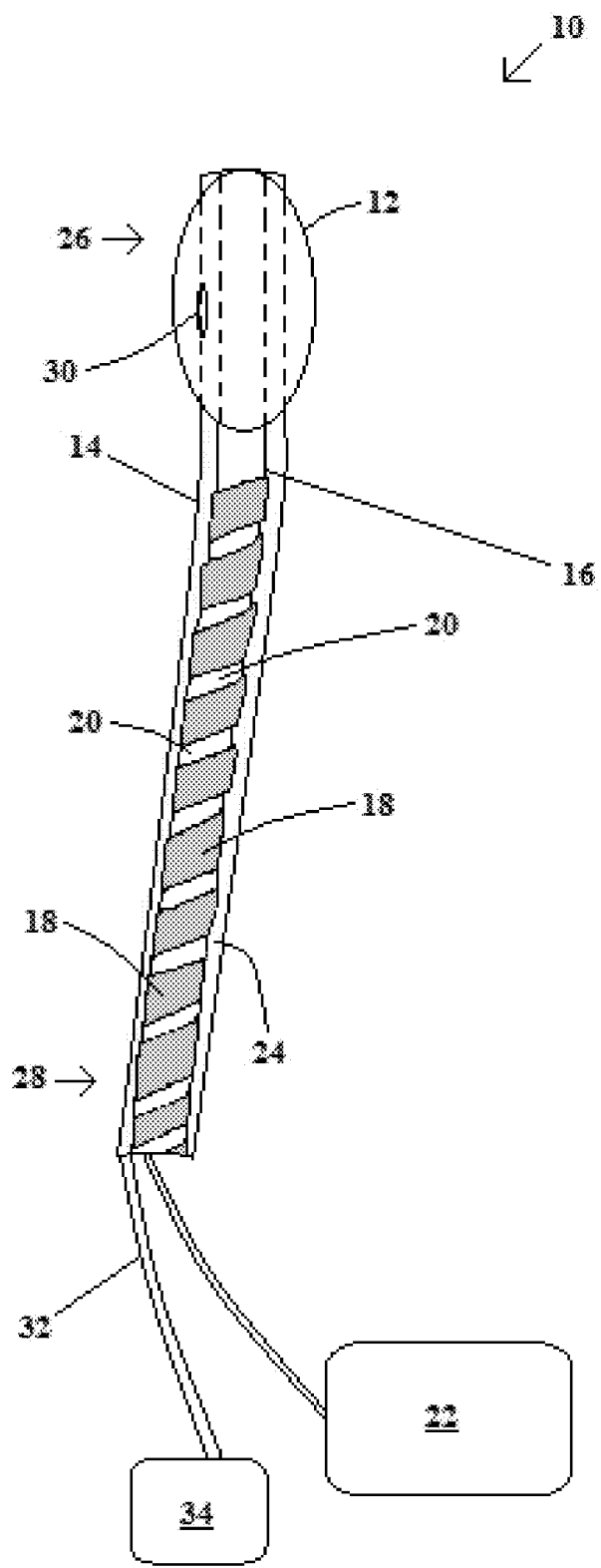
FIGS. 1A-1B: Partial cutaway illustration of an embodiment of an organ repositioner device designed for rectal repositioning (FIG. 1A), and illustration of the relative anatomical positions of the prostate, rectum, and bladder, and the benefits of repositioning of the rectum using a repositioning device (FIG. 1B).
Figure 1B:
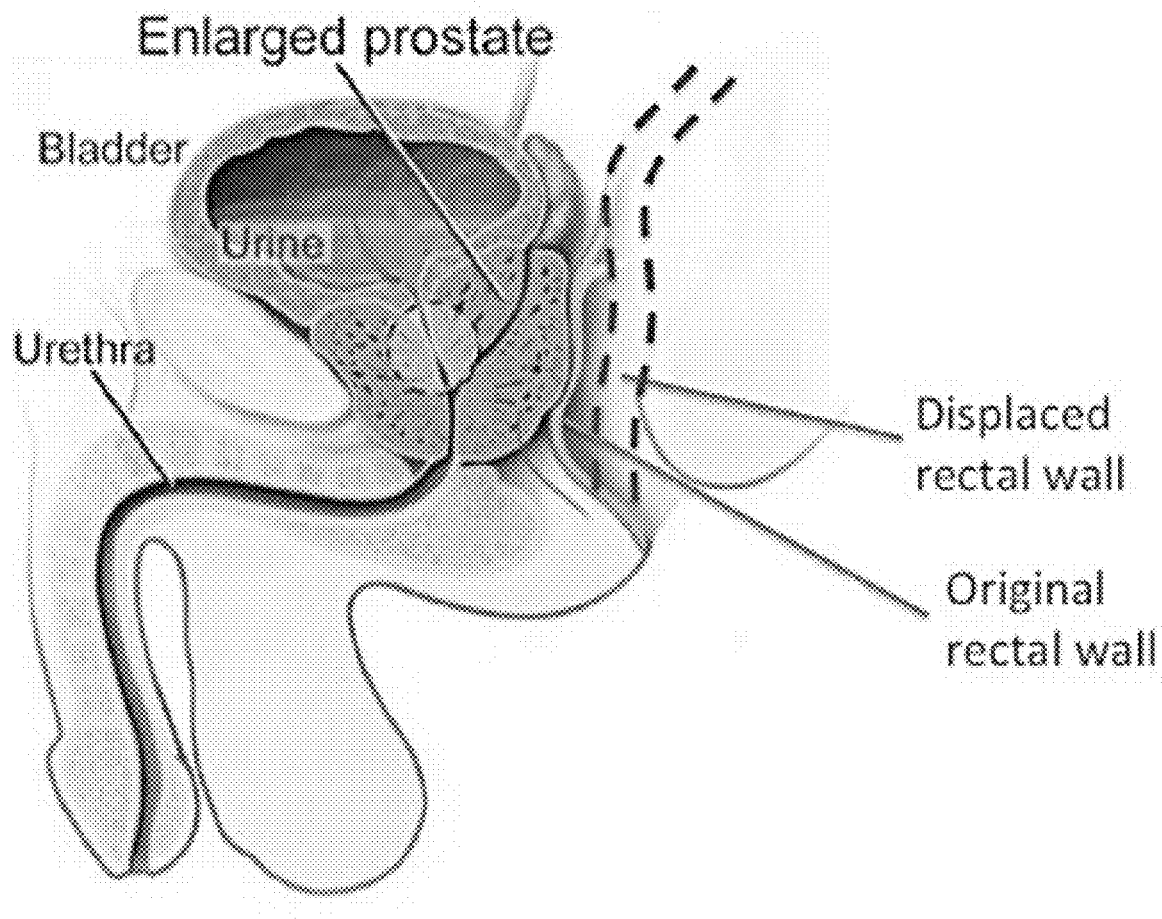

Provided is an organ repositioner device which, in some embodiments, is designed and fabricated to physically move the rectum away from the path of a direct radiation beam during external beam and bracytherapy treatments. FIG. 1A illustrates an embodiment of the organ repositioner device designed for rectal repositioning. Using the device, the rectal wall can be shifted away from the source of radiation, or from the vicinity of the radiation field, resulting in a lower dose to the rectum. When actuated, the organ repositioner device assumes a pre-defined shape that can apply pressure to the posterior wall of the rectum, resulting in displacement of the entire rectum posteriorly, away from the target volume. (FIG. 1B.) This allows for the delivery of an ablative SBRT dose to a tumor, or to escalate the dose when needed. Moving the rectum away even a short distance, such as 1 cm, from the plane of radiation can dramatically relax the prescription dose limitation. The organ repositioner device, by lowering the rectal dose in a convenient and easily reproducible manner, can serve an integral role in shorter-course treatment regimens, allowing dose escalation in a safe manner Minimizing the radiation dose to adjacent critical structures reduces the risk of treatment-related toxicities, and can greatly influence a patient's quality of life after treatment.

It is understood that, though rectal repositioning is described through the application for ease of illustration, the device and methods described herein can be utilized to reposition many other organs or anatomical structures. With respect to the rectum in particular, the organ repositioner device represents a shift in paradigm, as the current means of limiting rectal dose during prostate radiotherapy all fall far short of achieving permanent dosimetric gains. None of the current approaches appear to be practical and/or widely feasible in all clinical settings. Existing approaches to minimize rectal dose entail: utilizing the effect of gravity, using rectal balloons (which displaces the posterior wall of the rectum at the expense of exposing further the anterior wall), or the recently adapted invasive procedure by some clinics of insertion of temporary, gel-like dissolvable substrates in the region between the rectum and prostate, creating a few mm of space.

Figure 2A:
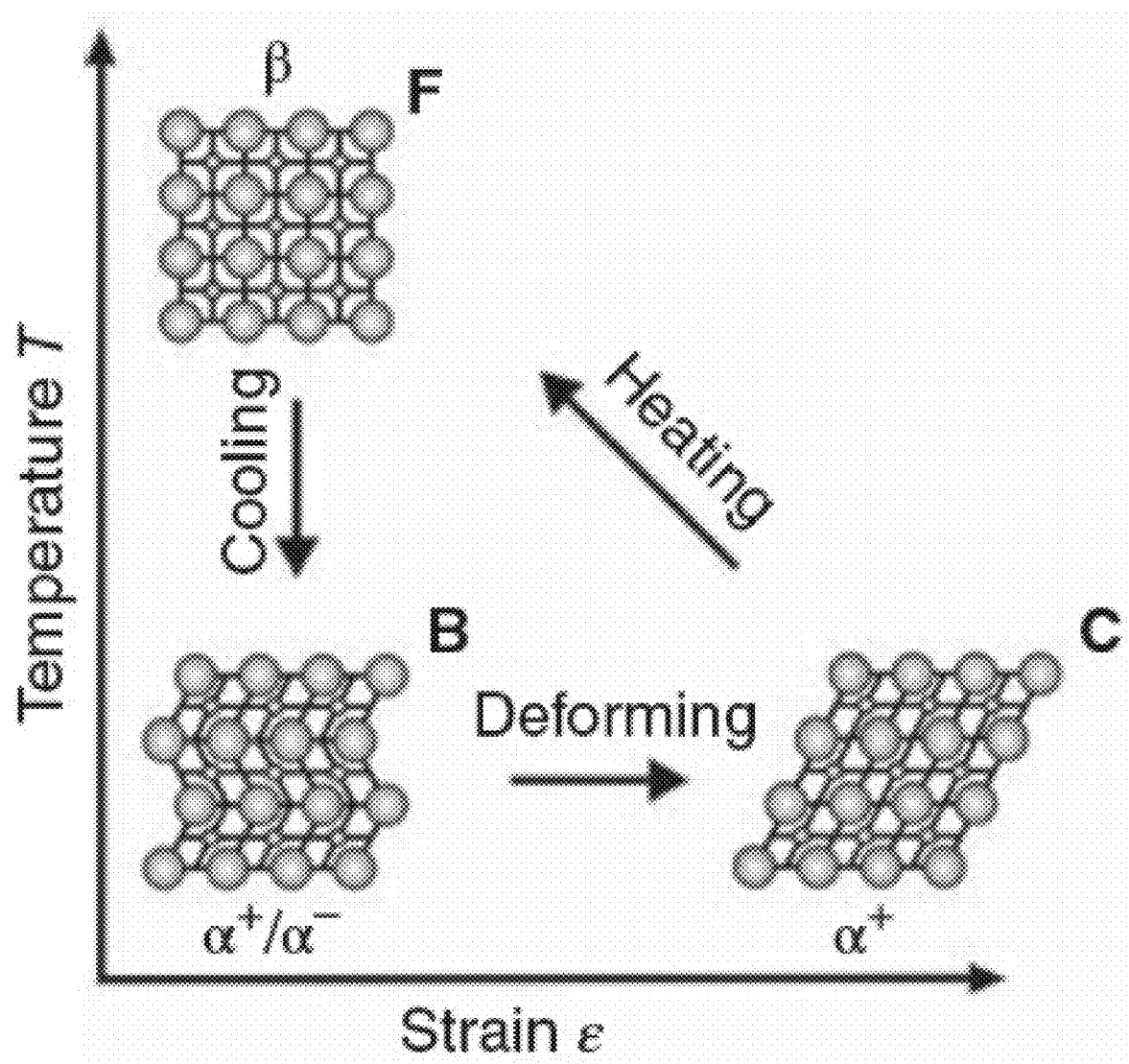
FIGS. 2A-2B: Shape memory effect path in stress-strain-temperature space.
Figure 2B:
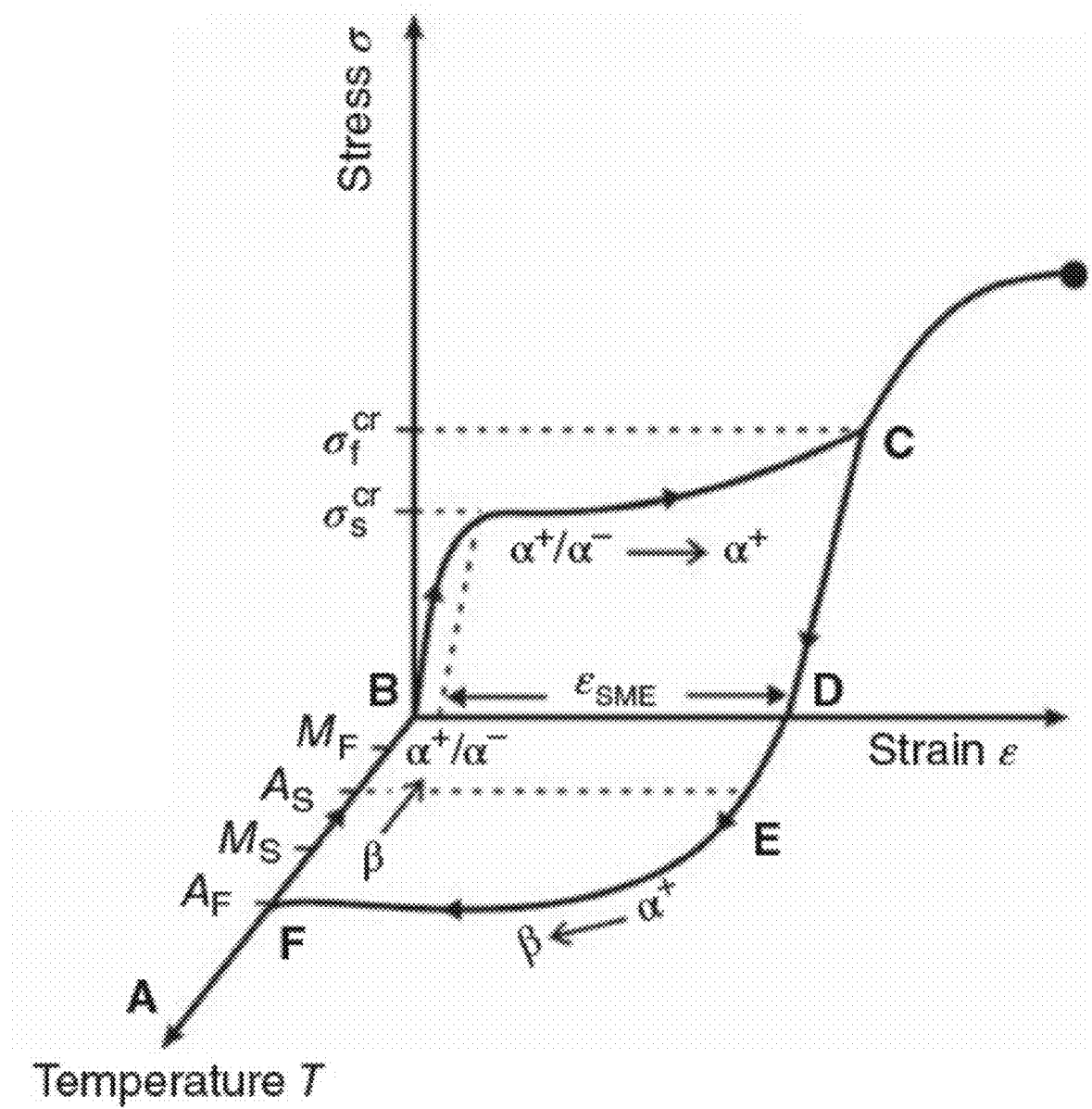

In general, the organ repositioner device includes components made of shape memory alloys (SMAs). Shape memory alloys are a class of smart materials that can recuperate their initial shape after being deformed mechanically. SMAs are distinguished from conventional metallic materials by their ability to restore their shape after large deformations, which can significantly exceed the actual elastic deformability of the material. This is referred to as shape memory effect (SME), characteristic as demonstrated in FIG. 2A. SME is the ability of these alloys to recover a certain amount of unrecovered strain upon heating, which takes place when the material is loaded such that the structure reaches the detwinned martensite phase and then unloaded while the temperature is below the austenite start temperature (As). SME occurs because of the transformation between martensite and austenite phase when subjected to thermomechanical changes. Heating the material at this stage to austenite will lead to strain recovery, and the material will regain its original shape. Shape memory alloys can thus recover their original shape by heating above the austenite transformation temperature when subjected to deformation at low temperature. The combined stress-strain-temperature diagram as shown in FIG. 2B illustrates this phenomenon. At lower temperature, the soft martensite phase is observed, which can be easily deformed. When this deformed SMA is heated beyond transformation temperature, phase transformation takes place, and austenite phase is obtained. After this phase transformation, the original shape is recovered. This property enables the shape memory alloy to be used as a unique actuator.

SMAs are useful in positioning surrounding tissue out of the area affected by a treatment. In most radiation oncology applications, the use of a shape memory alloy actuation can be beneficial in sparing the surrounding normal tissues and critical structures by simply relocating the structure away from the path of the external beam or place distance between the structure and source of radiation in cases of brachytherapy. Implementation of this device as an organ positioner in conjunction with IMRT and SBRT allows for dose escalation and significant dose reduction to normal tissues. Another example is during atrial fibrillation radio frequency ablation, where dysfunctional cells are ablated by heat and can cause thermal injury to the nearby tissue, namely the esophagus. By inserting an SMA-based repositioner device in the esophageal tube, surgeons can shift the esophagus away from the affected area.

A non-limiting example of a shape memory alloy is nitinol (NiTi). Nitinol is a binary alloy of nickel and titanium. Nitinol is implantable and capable of shape-setting via crystalline phase transformation in various geometries. Nitinol has one of the highest force-to-mass ratios of shape memory alloys. For example, a nitinol wire of radius 0.254 mm can lift as much as 7.257 kg. This, combined with other desirable properties such as maintainability and reliability with clean and silent actuation, makes nitinol an ideal actuator for various application. Nitinol is already accepted and used in the medical device community, for example as cardiovascular stents. Though nitinol is described for exemplary purposes herein, it is understood that the organ repositioning device can utilize shape memory alloys other than nitinol.

Figure 3A:
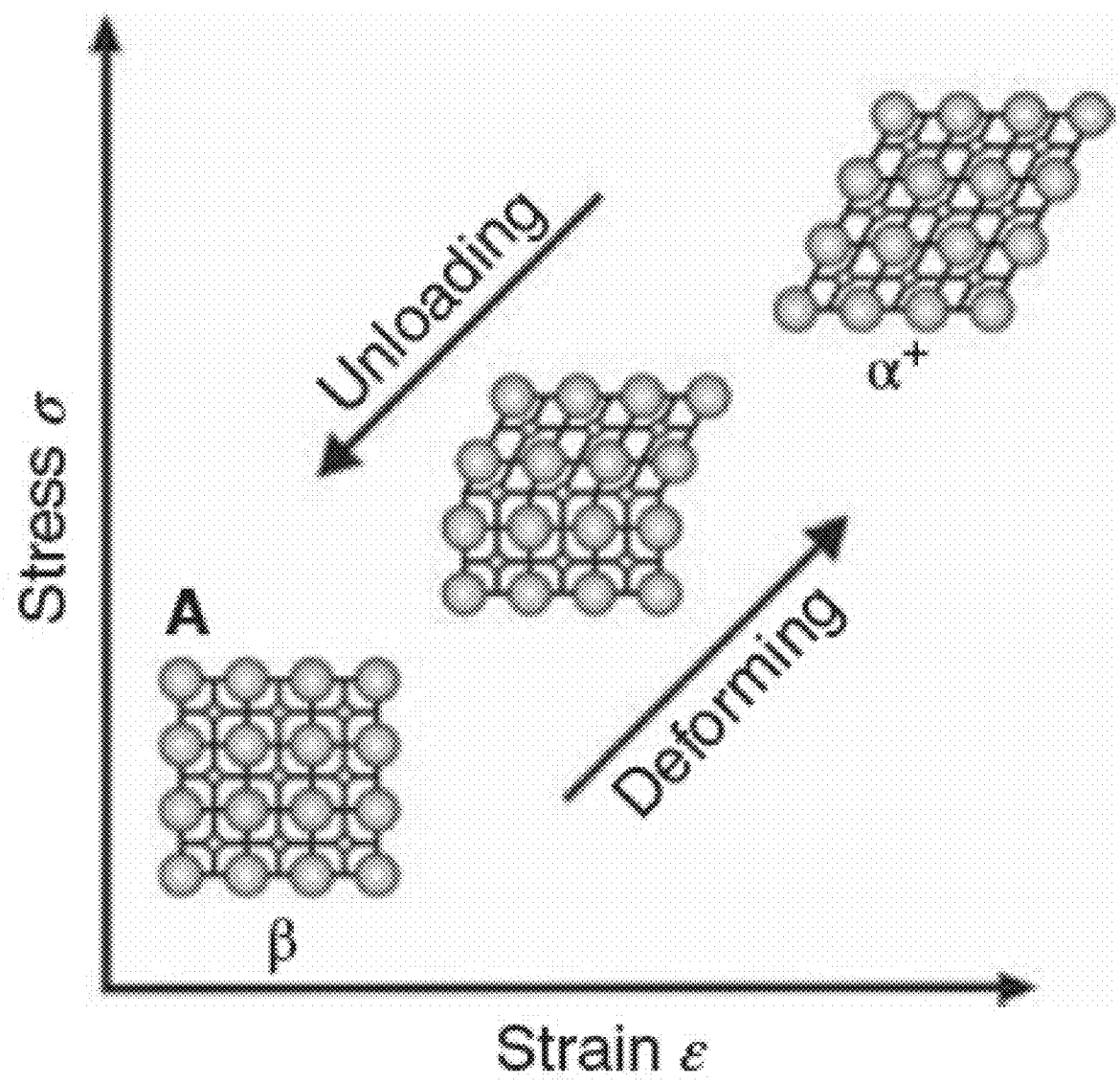
FIGS. 3A-3B: Schematic diagrams of superelasticity: effect of load on crystalline structure (FIG. 3A), and stress-strain-temperature plot (FIG. 3B).
Figure 3B:
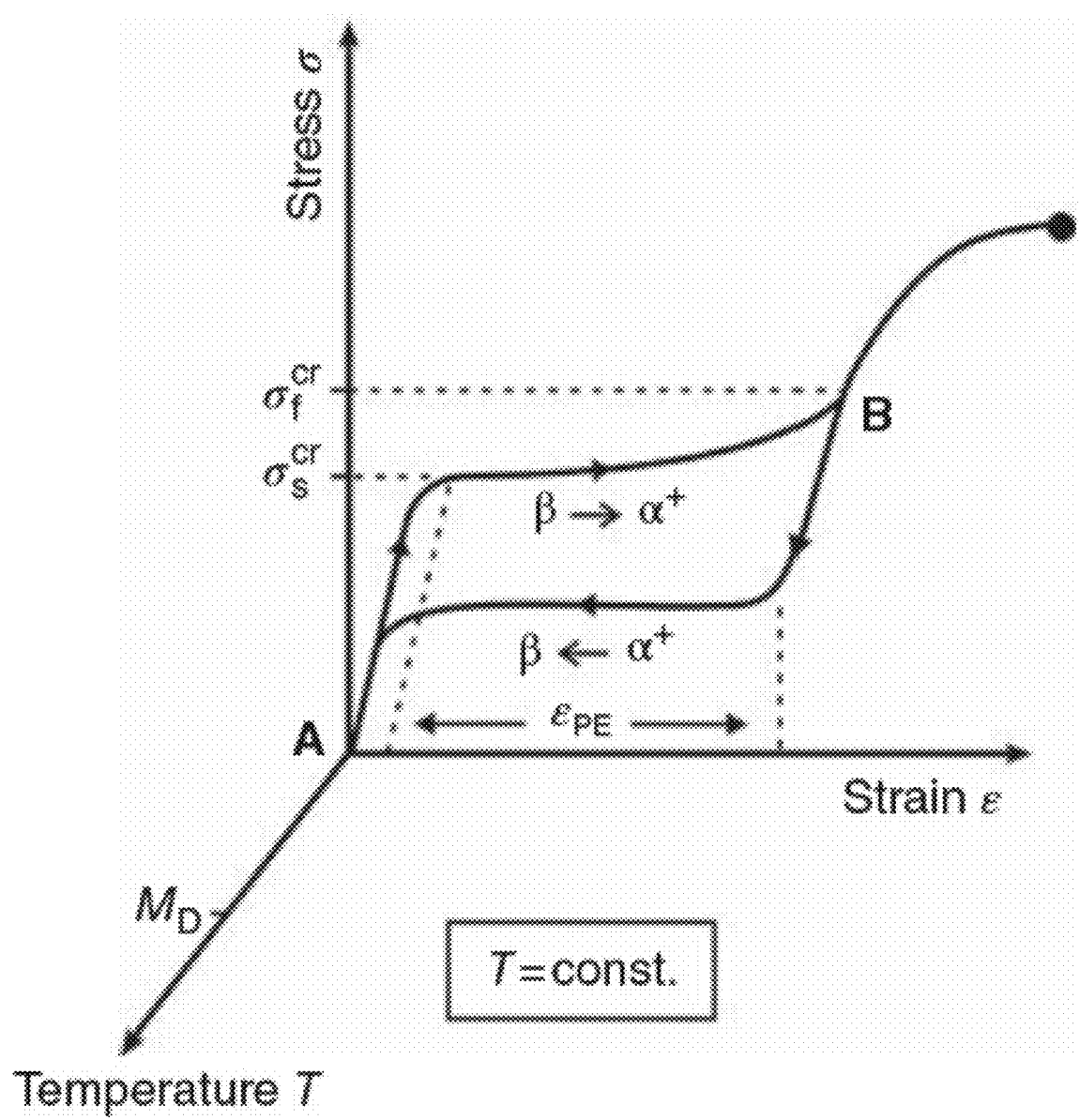

Nitinol exhibits both the shape memory effect and superelasticity (SE). As mentioned above, shape memory is the ability to undergo deformation at one temperature, then recover the original, undeformed shape upon heating above its transformation temperature. Superelasticity, on the other hand, occurs at a narrow temperature range just above the material's transformation temperature. In contrast to the thermally activated effects, in superelasticity, no temperature change is required. Instead, an external mechanical load can be used to induce phase transformation. In this phenomenon, the detwinned and favorably oriented martensite variants directly transform from the austenitic phase. As shown in FIG. 3, the superelastic behavior takes place at temperatures above the austenite finish temperature (Af) where the material is fully austenitic. As shown in FIG. 3B, loading the material from point A initially induces elastic deformation of the austenite phase. Further loading leads to stress-induced formation of the detwinned martensite crystal and the macroscopically elastic-like deformation of this structure to point B. The transformation strain generated during this forward transformation from austenite to martensite is fully recovered in the reverse transformation. This takes place during the unloading from point B, which involves an initial elastic recovery of martensite followed by the transformation to austenite and finally the elastic recovery of austenite to point A. At this point, the strain is completely recovered. Thus, for superelasticity, no heating is necessary to cause the undeformed shape to recover, and the material exhibits more elasticity than ordinary metal.

By varying the atomic percentage of nickel and titanium in the alloy, the resulting shape memory alloy can be made to be either an SM element or an SE element. As described herein, an organ repositioner device includes an assembly of an SM element and an SE element. In general, certain nitinol alloys can exhibit shape memory or superelastic behavior, or both. Although nitinol is essentially a binary alloy with nickel and titanium, some superelastic and/or shape memory Ni:Ti alloys can contain additional elements, such as cobalt or vanadium. In addition, some other alloys exhibit shape memory or superelastic behavior or, like some Ni:Ti alloys, both shape memory and superelasticity. Some examples of these alloys are: AgCd, AuCd, AuCu, CuAlNi, CuAuZn, CuSn, CuZn, CuZnSi, CuZnSn, CuZnAl, CuZnGa, CuZnXe, CuAlNi, InTl, NiAl, FePt, FePd, FeMn, $Fe_3Be$, $Fe_3Pt$, FeNiTiCo, and MnCu. Some polymers and other materials have also been shown to exhibit shape memory or superelastic behavior, or both. It is understood that the organ repositioner device described herein can utilize any combination of these materials, so long as the device includes an assembly of a shape memory element and a superelastic element. NiTi is especially useful, however, for actuation and motion control applications because NiTi can be easily heated by passing an electrical current while offering several advantages for system miniaturization such as high power-to-mass ratio, maintainability, reliability, and clean and silent actuation.

Figure 4:
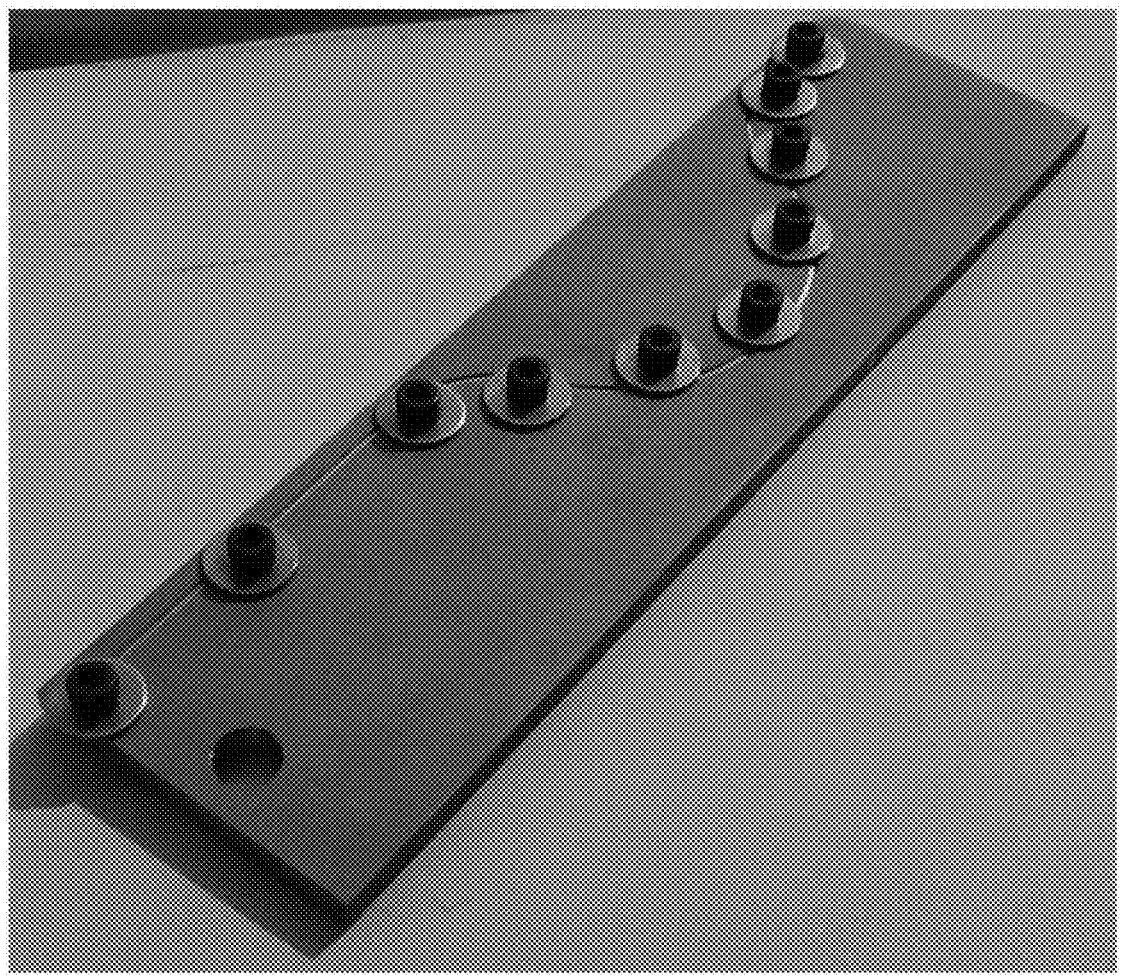
FIG. 4: Photograph of a shape-setting jig used for securing the NiTi wire during the heat treatment.
Figure 5:
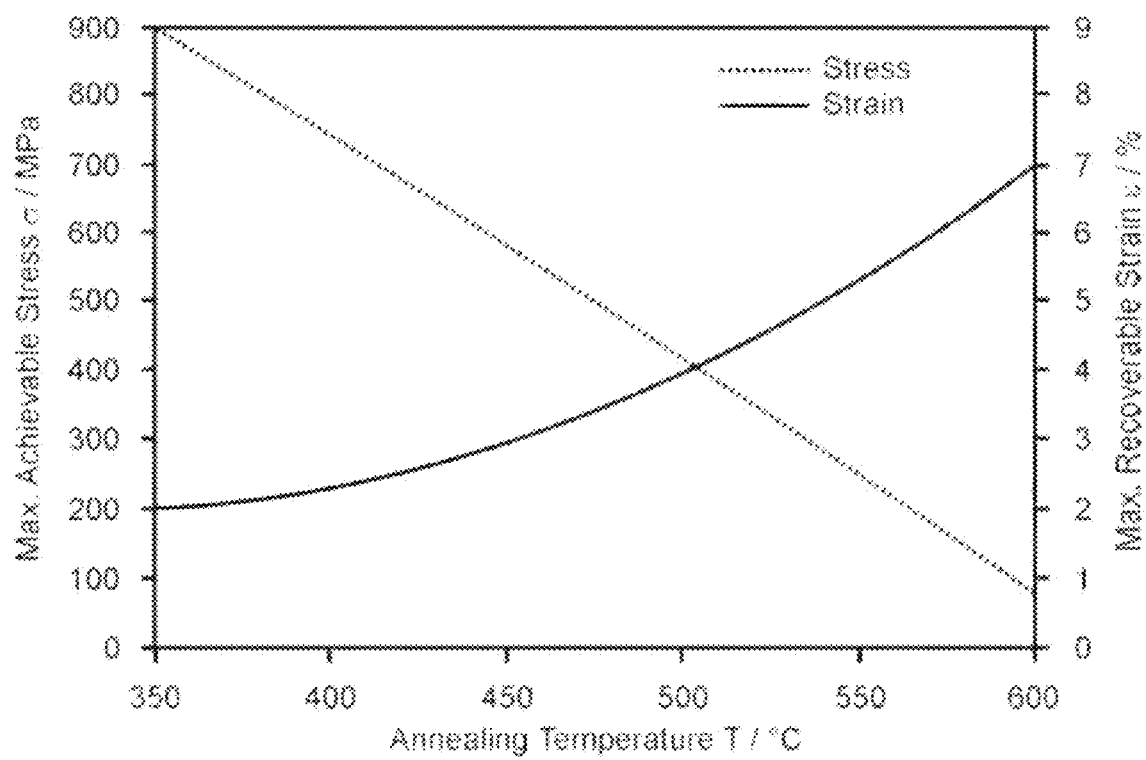
FIG. 5: Schematic showing the correlation of annealing temperature for shape setting (t=30 min) of a NiTi actuator, and maximum achievable stress of this actuator in case of suppressed deformation and maximum recoverable strain in case of free shape recovery, respectively.

Semi-finished SMAs such as wires require a shape set configuration to reveal the demanded functional properties before being used in their desired application. This configuration is accomplished by a special heat treatment called shape setting. The objective of this treatment is to improve the shape recovery behavior since cold-worked NiTi does not exhibit shape memory properties, and to establish the geometrical shape, which is memorized in the shape memory operations. For this heat treatment, the semi-finished product such as a wire or a sheet is cold-formed on a jig into the final product shape, as shown in FIG. 4. This cold-deformation requires a significant amount of deformation beyond the recoverable limit because of the large springback effect in NiTi or superelastic shape recovery. In this constrained shape the NiTi has to be fixed tightly on the jig, for example with screws or by using a tight fit. The suppression of free recovery results in the buildup of stresses within the material, which later will relax in the course of the following shape setting heat treatment. The shape setting heat treatment can be performed at moderate conditions but the temperature should be about 350-450° C. higher than the austenite-finish temperature of the alloy. Temperature and duration may vary slightly to account for the desired application and geometry (wire, strip, ribbon, sheet, etc.) but both significantly affect the shape recovery properties, mechanical behavior, and transformation temperatures of the material. As shown in FIG. 5, shape setting at low temperatures results in low recoverable strains, but if the deformation is suppressed high forces can be achieved because work hardening effects are mostly retained. In addition, shape setting at low temperatures also results in higher fatigue life. In contrast, shape setting at higher temperatures results in higher recoverable strains but achievable forces and fatigue life decrease.

The organ repositioner device has two shapes, which can be referred to for purposes of illustration as shape 1 and shape 2. The following explains a non-limiting example of the functionality of the device. The device is in shape 1 at the time of insertion. Thus, before insertion, the SMA in the device is unactuated (i.e., martensitic phase). After insertion, the device gradually changes to shape 2 (its pre-determined shape, i.e., austenite phase), either by active or passive heating or cooling. The SMA in the device is actuated in order to move the rectum away from the radiation field. The device maintains shape 2 during the treatment session. In some cases, the actuation causes the repositioner device to be positioned next to the posterior wall of the rectum. The repositioner device pushes the posterior rectum wall, which in turn moves the anterior rectum wall towards the posterior wall. Before removal, the organ repositioner device reverts back to shape 1 for easy removal. The shape changes are the result of temperature variation, which can be actively controlled via electric current or passively caused by body temperature. The temperature of the surface of the device does not exceed the safe temperature of 40° C. The motion is gradual to minimize the risk of injury. The maximum deflection of the device is limited to not cause any injury. Optionally, the device can be marked for reference such that the device is inserted with the markings pointed towards the posterior rectal wall, for ease of use.

The length of interest for the rectum is about 20 cm. That starts from posterior part of the external anal sphincter muscle to about where the rectosigmoid junction begins. The prostate, which is typically the organ that is intended for irradiation, is usually located in the middle of this length. In some embodiments, the organ repositioner device moves the wall of the rectum from where the prostate gland is by about 2 cm, though it is understood that the ideal length varies based on the patient's anatomy. In the 20 cm long device, the prostate is generally located at about 10 cm from the anus. In some embodiments, the displacement takes place starting from about the 5 cm point to about the 10-12 cm point along the rectal repositioner device.

The functionality of the organ repositioner device is achieved by combining the properties of a shape memory and/or a superelastic element as explained below. Active heating can take place either by directly passing a controlled current through the device or by passing controlled current through an external heating element that is wrapped around the SMA elements.

One embodiment is based on combining a superelastic round wire and a flat shape memory wire by wrapping the flat wire around the round wire. In this embodiment, the shape memory flat wire is shape set to assume shape 2 and the round superelastic wire is shape set to shape 1. At low temperature the assembly assumes shape 1 and at high temperature the assembly assumes shape 2. At an intermediate temperature, the assembly has an equilibrium shape between shape 1 and shape 2. In this configuration, the assembly is heated for the duration of the treatment but not for insertion and removal. Another embodiment is based on combining a superelastic round wire and a flat shape memory wire by wrapping the flat wire around the round wire. In this embodiment, the shape memory flat wire is shape set to assume shape 1 and the round superelastic wire is shape set to shape 2. At low temperature the assembly assumes shape 2, and at high temperature shape 1. At an intermediate temperature, the assembly has an equilibrium shape between shape 1 and shape 2. In this configuration, the assembly is heated for insertion and removal. The skilled person will recognize that the combination of an SM element and an SE element is versatile and customizable in many different ways.

The variation of electrical resistance is significant during phase transformation. By using the variation in electrical behavior during the phase transformation to determine the strain of SMA, the need of an external sensor in a feedback control is eliminated. While heating the wire, the resistance of the actuator can be monitored to measure the level of displacement in the device. Light indicators on a control unit can show the level of displacement based on the value of the electrical resistance. This is an additional assurance measure as imaging techniques are used to ensure the proper positioning for treatment. In some embodiments, a controller unit adjusts the level of current to the SMA actuator. The controller can have two modes of operation: manual and automatic. In the automatic mode, the operator selects the level of displacement needed. The control unit can adjust the current applied to the actuator to achieve the desired level of displacement while monitoring the electrical resistance of the SMA elements. In the manual mode, the operator adjusts the current applied to the SMA elements to achieve the desired level of displacement by continuously monitoring the electrical resistance.

In some embodiments, the repositioner device employs both of the two properties of SMAs: shape memory effect and superelasticity. An SM member when combined with an SE element creates an antagonistic actuator. The SM segment controls the actuation function, while the system is designed and operated in a way that the SE element provides the opposing actuation force and stroke. Actuation generally works best between two temperatures, referred to for ease of reference as a high temperature and a low temperature. The SE member is always in the austenite phase; that is, its austenite finish temperature is lower than both the high temperature and the low temperature. On the other hand, the SM element is initially in its martensite phase, which transforms to austenite at high temperature. To this end, the SM material should be selected such that its matensite finish temperature is below the low temperature and its austenite finish temperature is below the high temperature. The geometry of the SE and SM components and their memorized shape are set such that in low temperature, the memorized shape of the SE element is stronger and the assembly moves toward the SE element, which is designed to be the low-temperature (inactive) form of the actuator. At the high temperature, the SM segment exceeds its austenite temperature and deflects the assembly toward its memorized shape that is designed to be the high temperature (active) configuration of the device.

Figure 6A:
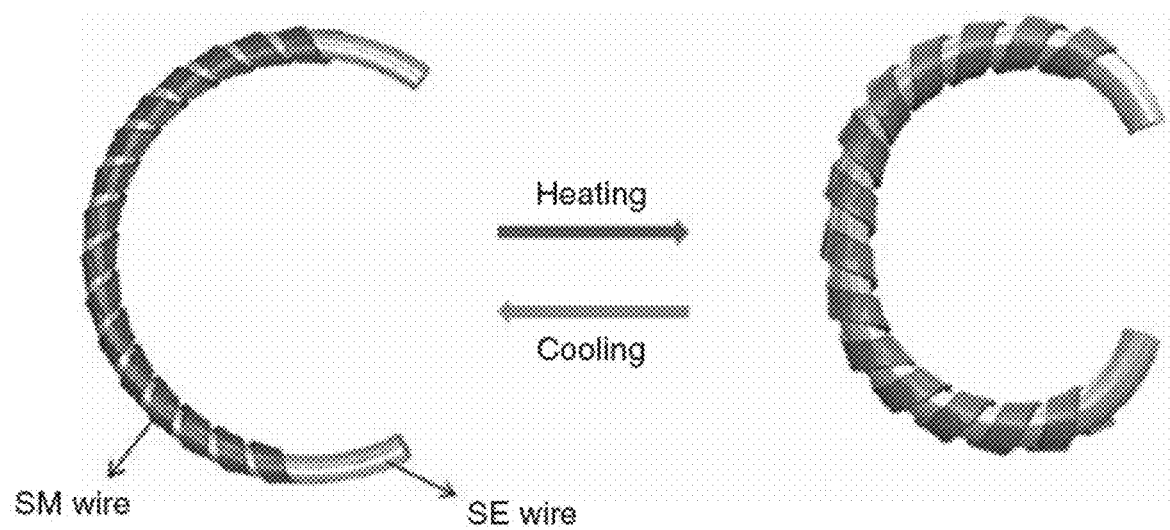
FIG. 6A: An antagonistic superelastic wire and shape memory flat wire wrapping creates a bistable actuation mechanism. Low temperature (left) and high temperature (right) stable forms provide the close and open forms of the actuator.

FIG. 6A illustrates an assembly that combines a superelastic round wire with a flat shape memory wire. In this embodiment, the SM element is a flat wire and the SE element is a ring shaped round wire. By wrapping the flat wire around the round SE member, an antagonistic actuator is formed. When the two members are assembled at a low temperature, they apply force on each other in a way that the SM wire tends to close the ring. Depending on the material properties, geometry, and the memorized shape of each of the two components, an equilibrium shape will be obtained at the low temperature. The left side of FIG. 6A displays the equilibrium or neutral position of the assembly at low temperature. By heating the SM element either by changing the thermal environmental conditions or by resistive heating, the assembly moves toward the shape set form of the SM member, which tends to close the ring, as shown on the right side of FIG. 6A. By cyclic heating and cooling, these two configurations can be repeated. It is understood, however, that the actuation stroke and shape generally depend on the geometry, material properties, and shape set forms of the SM and SE elements; thus, numerous actuation configurations are possible with the antagonistic actuator created by an assembly of SM and SE elements.

Figure 6B:
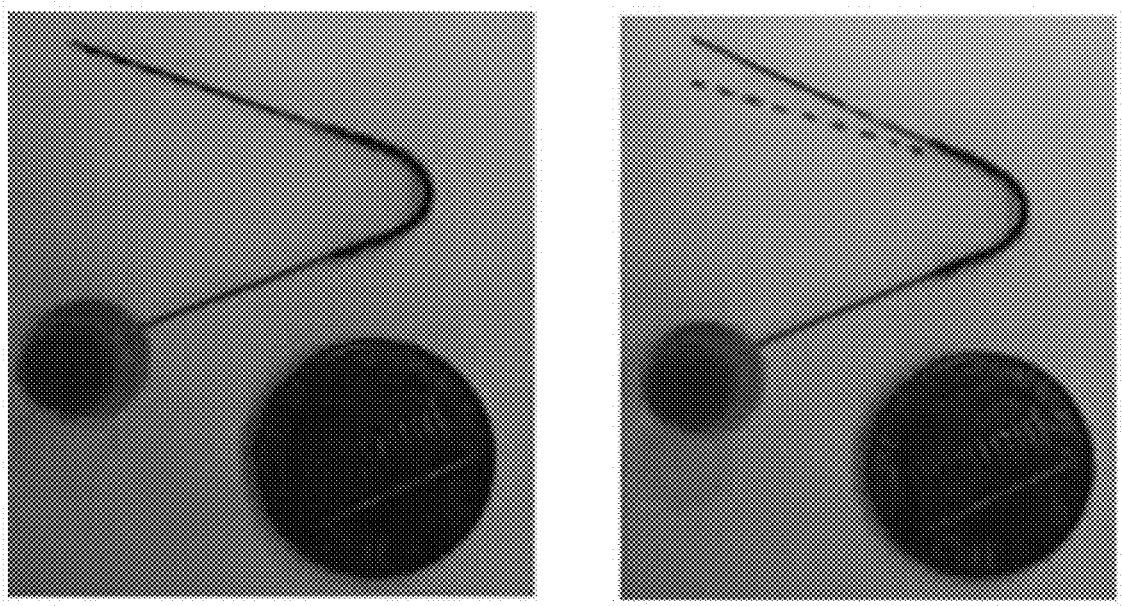
FIG. 6B: An antagonistic superelastic flat wire wrapped around a shape memory wire creates a two-way actuation with repeatable actuation between two stable positions: low-temperature (left) and high-temperature (right) positions. A penny is shown for scale.

FIG. 6B shows a similar configuration where an actuator is created from a flat superelastic wire, which is wrapped around a SM wire to create a bidirectional bistable actuation.

To make an assembly such as shown in FIGS. 6A-6B, the two elements are shape set in the desired configurations that they should assume. When the two elements are in contact in the final assembly, the antagonistic actuator assumes a neutral position. At high temperatures, the SM element transforms to austenite, meaning the flat wire becomes stiffer. The higher stiffness should be sufficient to deform the superelastic round wire. At higher temperatures, the stiffness of the SM flat wire should be greater than the stiffness of the round SE wire. On the other hand, at the low temperature, the stiffness of the round SE wire should be greater than the stiffness of the SM wire. As soon as the SM wire is heated, it starts to actuate.

The organ repositioner device can be created by an assembly of SE and SM elements used as an alternative insert to existing endo-rectal devices. As shown in PRIOR ART FIG. 7A, a commercially available rectal positioner device is a balloon-based marker used for prostate fixation and to localize the rectum during the radiation treatment. However, this device has the potential to increase the chance of rectal toxicity as it causes the anterior rectal wall to be pushed against the prostate, which is the target, and in the direct field of the radiation. As an example of application, the repositioner device described herein can be an insert of the device shown in PRIOR ART FIG. 7A to provide the desired functionality of moving the rectal wall away from the prostate during the radiation therapy treatments.

Figure 7B:
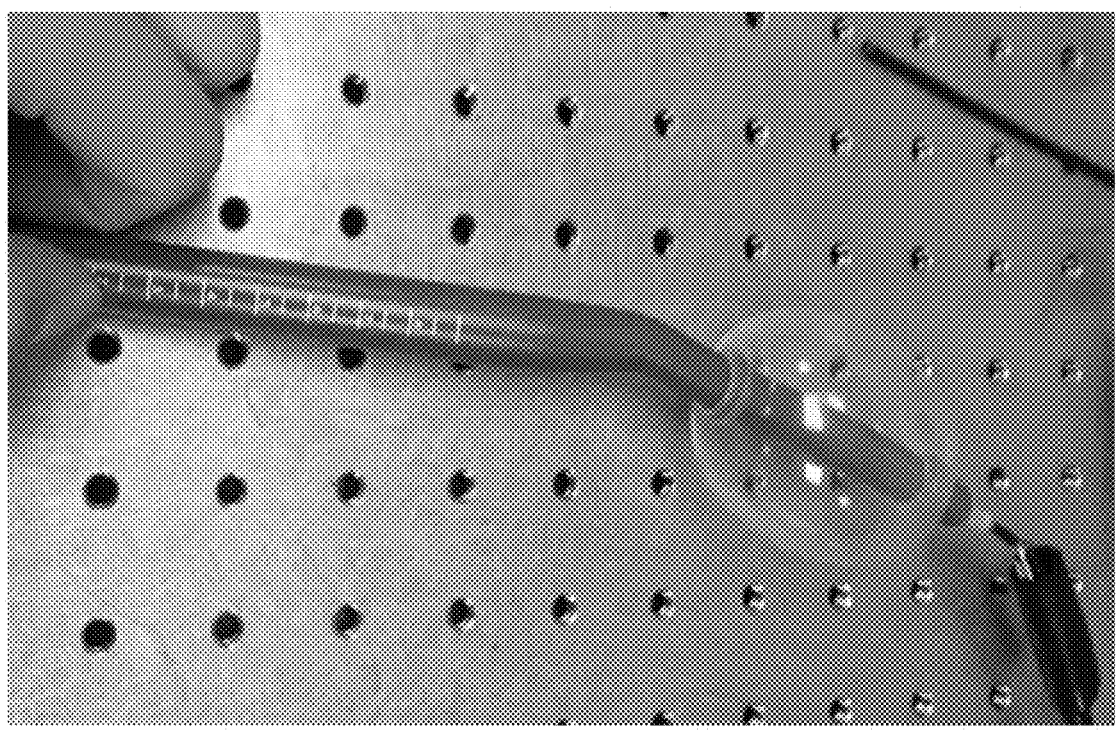
FIG. 7B: Color photograph of an organ repositioner device that includes an endorectal balloon. The organ repositioned device can move the inflated rectum away from the prostate and out of the radiation beam path.
Figure 7C:
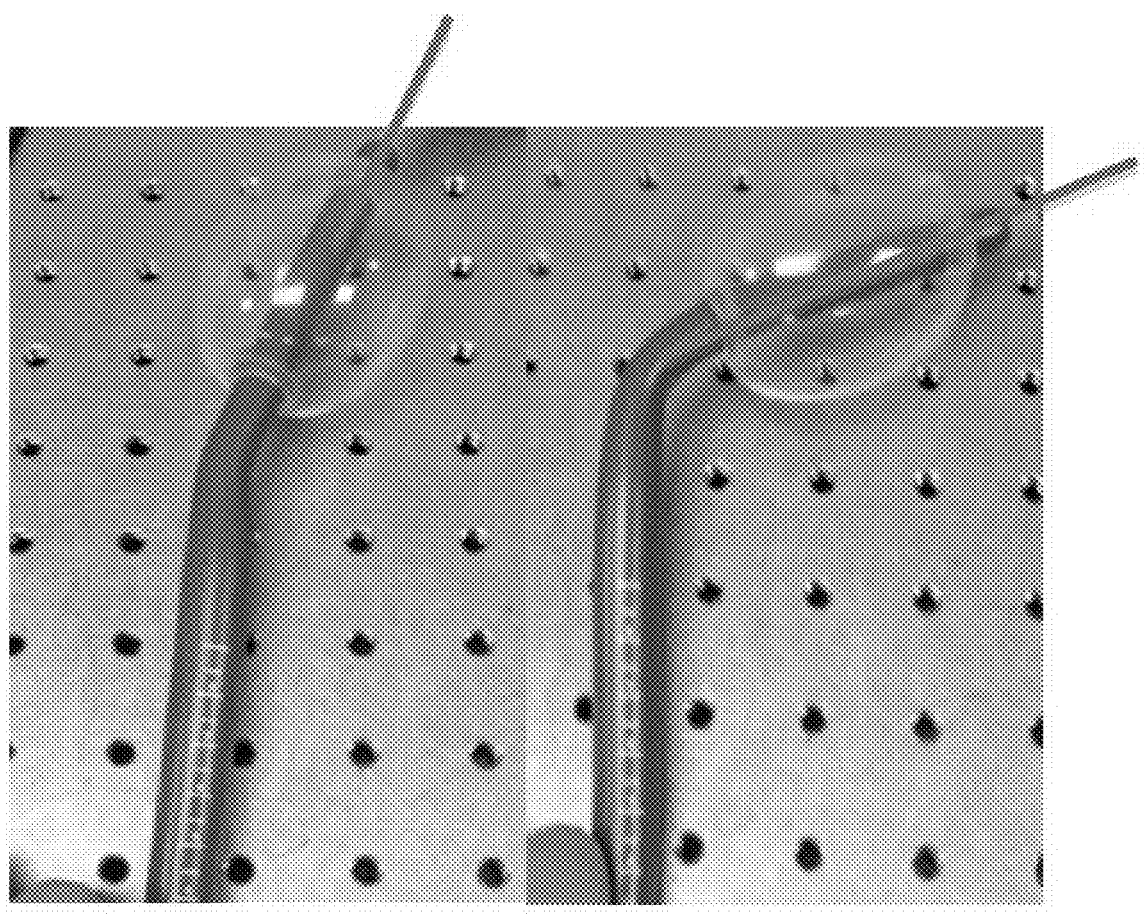
FIG. 7C: Color photographs of an organ repositioner device with two shapes: shape 1 (left) and shape 2 (right). In this example, the device has 55° of rotation from the initial configuration. Blue lines are shown as guides to illustrate the degree of rotation.

FIGS. 7B-7C show photographs, and FIG. 1A shows an illustration, of an embodiment of the organ repositioner device where an assembly of SM and SE elements is an insert of an endorectal balloon device such as that shown in PRIOR ART FIG. 7A. As seen from FIG. 1A and FIGS. 7B-7C, the organ repositioner device 10 includes an inflatable endo-rectal balloon 12 mounted on a bendable tube 14 which defines a lumen 24. The tube 14 has a proximal end 26 and a distal end 28. The balloon 12 is mounted on the proximal end 26 of the tube 14. In some embodiments, the organ repositioner device includes multiple balloons 12, such as semispherical balloons, mounted on the tube 14. The organ repositioner device 10 can include an opening 30 at the proximal end 26 of the tube 14 connected to an air supply line 32 configured to deliver air from an air source 34 so as to inflate the balloon 12. It is understood that the air source 34 need not be external to the device; rather, the air source 34 can be a small cartridge that fits inside the lumen 24. Alternatively, the air supply line 32 can be connected to any source of pressurized air.

The lumen 24 houses an assembly 16 of the SM element 18 and the SE element 20 formed together. The SM element 18 has a first shape set form, and the SE element 20 has a second shape set form. Either the SM element 18 is formed around the SE element 20, or the SE element 20 is formed around the SM element 18. For example, the SM element 18 can be a wire wrapped around the SE element 20 wire, or vice versa. Though FIG. 1A depicts the assembly 16 as extending the length of the lumen 24, from the proximal end 26 to the distal end 28, the assembly 16 need not extend through the entire lumen 24. Rather, it is only important that the assembly 16 extend through enough of the lumen 24 so as to cause the bendable tube 14 to bend upon actuation of the assembly 16. In other words, the bendable tube 14 bends upon shape transformations of the assembly 16.

The assembly 16 has an equilibrium shape between the first shape set form and the second shape set form. Upon heating and/or cooling, such as through an electrical current, the assembly 16 is actuated and the bendable tube 14 bends accordingly. As seen from the photographs in FIGS. 7B-7C, the organ repositioner device 10 can utilize the preformed bend in the endorectal balloon device for actuation. In the example shown in FIG. 7C, the organ repositioner device bends 55° from the initial configuration. Alternatively, the bendable tube 14 could be made to bend at an additional or alternative location upon actuation of the assembly 16. The bending of the bendable tube 14 can reposition the desired organ into the desired location, such as away from the path of a radiation beam. For example, in use for repositioning a rectum during a prostate treatment, the proximal end 26 of the organ repositioner device 10 is inserted in the rectal cavity, where the balloon 12 is then inflated to stabilize the prostate, and the assembly 16 is actuated. Actuation of the assembly 16, by heating or cooling (whether by active control or through passive heating/cooling caused by body temperature), causes the bendable tube 14 to bend and exert a pushing force on the rectal wall, thereby repositioning the rectum as desired.

The organ repositioner device 10 can further include a controller 22 for controlling the actuation of the assembly 16 as described below. The controller 22 is in electrical communication with the SM element 18 and the SE element 20. The controller 22 can apply a voltage in the device 10, and can determine the state of actuation by measuring electrical resistance in the device 10. The controller 22 is generally configured to apply a voltage to the device in a closed loop feedback based on the measured electrical resistance. By heating and/or cooling and measuring the resistance of the device 10, remote device displacement of an organ is possible with the device. Electronic circuitry on the controller 22 can give an indication of a safe range of displacement based on the feed value of the resistance. Changing the power input manually can allow safe and optimal dislocation of rectal tissue away from the field of radiation. The controller 22 can be configured to monitor the electrical resistance in the device, determine the actuation state of the device based on the measured actuation state, and control the voltage as necessary based on the determined actuation state.

As noted above, a shape memory alloy's resistance changes during transformation. In fact, the variation of electrical resistance during phase transformation is significant. Therefore, the change in resistance and other electrical properties can be used to sense the deformation of the material. The variation in electrical behavior during the phase transformation can be used to determine the strain of the shape memory alloy. In other words, the actuation state can be monitored by measuring the electrical resistance in the device. This eliminates the requirement of external sensors in a feedback control. Despite this ability of shape memory alloys, the phase transformation exhibits hysteresis behavior which acts as a drawback in using this self-sensing property in an SMA-based actuator.

There are two ways for modeling hysteresis. In the first method, a mathematical model is developed to model phase transformation and hysteresis behavior. Various phenomenological models have been proposed for this purpose. However, these constitutive models are based on experimentally determined parameters and approximations, which may not be suitable for online control system. Others have applied the Preisach model to capture hysteresis in SMA. However, these models involve complex equations with multiple parameters that are difficult to implement in a control scenario.

An alternative method is based on machine learning (ML) techniques, where experimental data are collected. An artificial neural network (ANN) is an example ML technique that is useful for SMA hysteresis modeling. As demonstrated in the Examples herein, an artificial neural network can accurately model the relationship between the electrical properties and manipulator position. However, it is understood that the device need not be used with an ANN.

The NiTi shape-setting can be optimized through cooling and heating the core alloy. The device may include an electronic circuit designed to induce the reversible NiTi austenitic transformation. In use, the motion of the repositioner device can be fully controlled in order to safely relocate the rectum during radiation treatment. Passive heating from the body can be utilized to cause the actuation. Alternatively, active heating can be applied to the device through an electrical current. As another alternative, the device can be fabricated such that cooling, instead of heating, causes the desired actuation. In such cases, the device can be heated prior to insertion, and allowed to cool inside the body to cause the desired actuation. The SMA materials provide great flexibility for customization of the device.

The organ repositioner device can be made in varying lengths of from about 10 cm to about 40 cm. The organ repositioner device can be manufactured to accommodate different rectal sizes through the use of expandable balloons in the distal part of the actuator, and is clinically comfortable during insertion and removal, as the device remains very flexible pre-actuation. The device can be marked at, for example, 1 cm intervals to provide a convenient reference to compensate for film or digital imaging magnification. When used for rectal repositioning, the device may or may not be used with an anus locator during X-ray imaging. The location of the device and the location of the organ being treated can be determined using conventional OBI device or even MV imaging onboard most accelerators.

EXAMPLES

This Example describes a system for controlling the methodology of a shape memory alloy-actuated rotary manipulator using the feedback signal from the artificial neural network model, thus eliminating the need for any external position sensor. The control methodology using a variable structure control technique was experimentally tested under different conditions. Also, the effect of environmental temperature on the ability of artificial neural network to predict manipulator position was analyzed using phenomenological model simulations. It is concluded that this system gives a robust performance with a small tolerance (less than 5°) and can operate well even when the ambient temperature changes considerably.

A robust position control methodology was developed using an internal feedback from ANN. An accurate ANN model was used to determine the manipulator angle from the electrical properties of SMA. First, the ANN-determined position was used as a feedback signal to control the SMA-actuated rotary manipulator. The control system was experimentally tested under various scenarios to determine the robustness of the proposed system. Then, the effect of ambient temperature was analyzed as it was found to play an important role in SMA actuation control. To analyze this, an approximate phenomenological model was used to simulate the rotary manipulator system, and the effect of ambient temperature on the performance of ANN is analyzed.

Device Design

Figure 8:
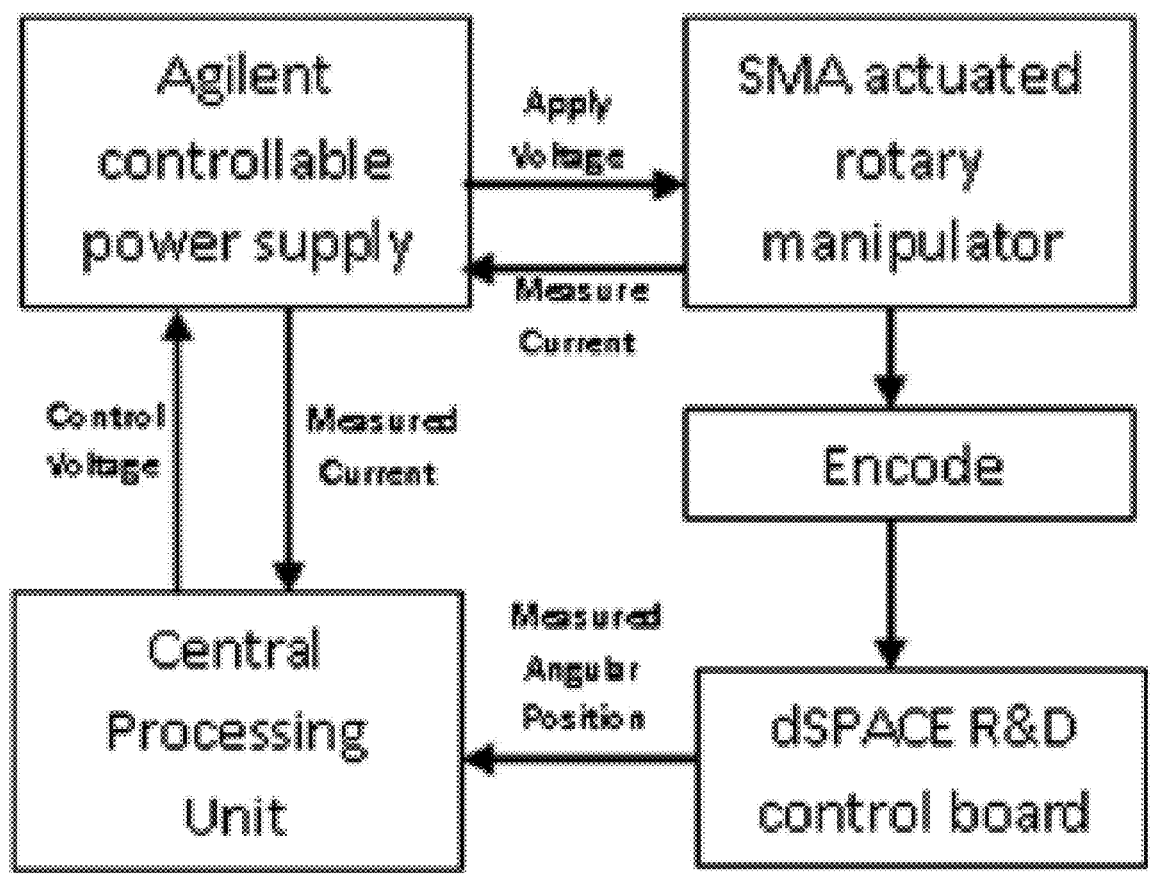
FIG. 8: Block diagram of the experimental setup described in the Examples herein.
Figure 9:
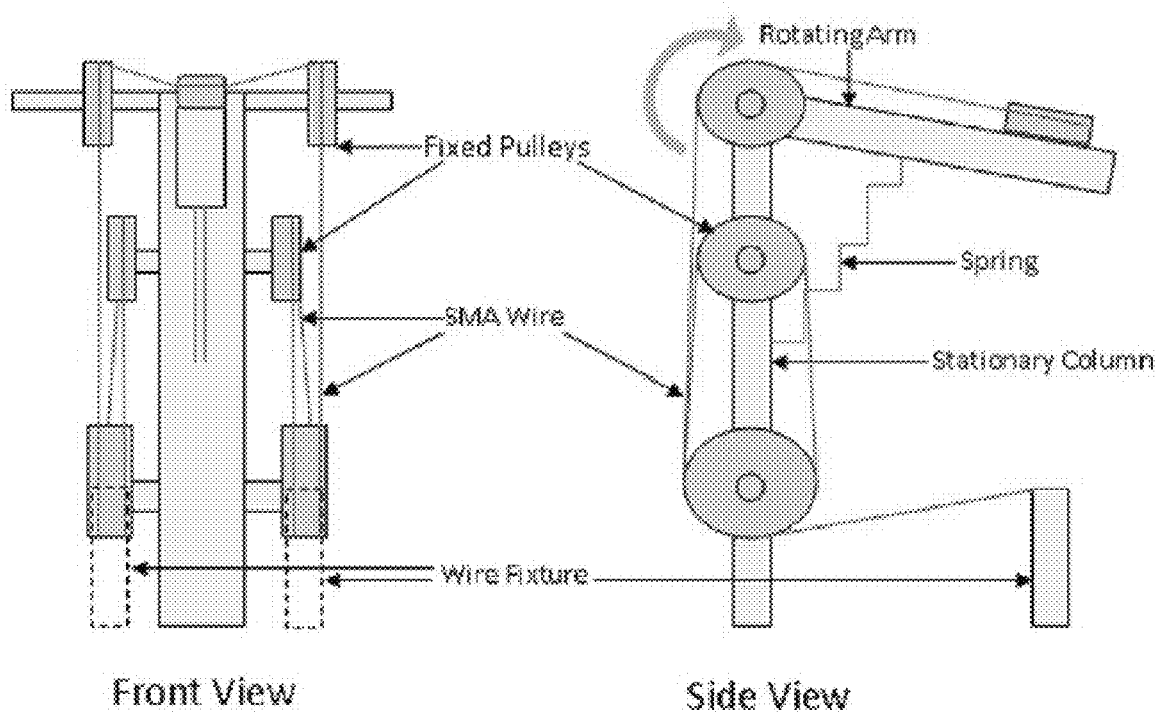
FIG. 9: Diagram showing components of SMA-actuated 1-DOF rotary manipulator.
Figure 11:
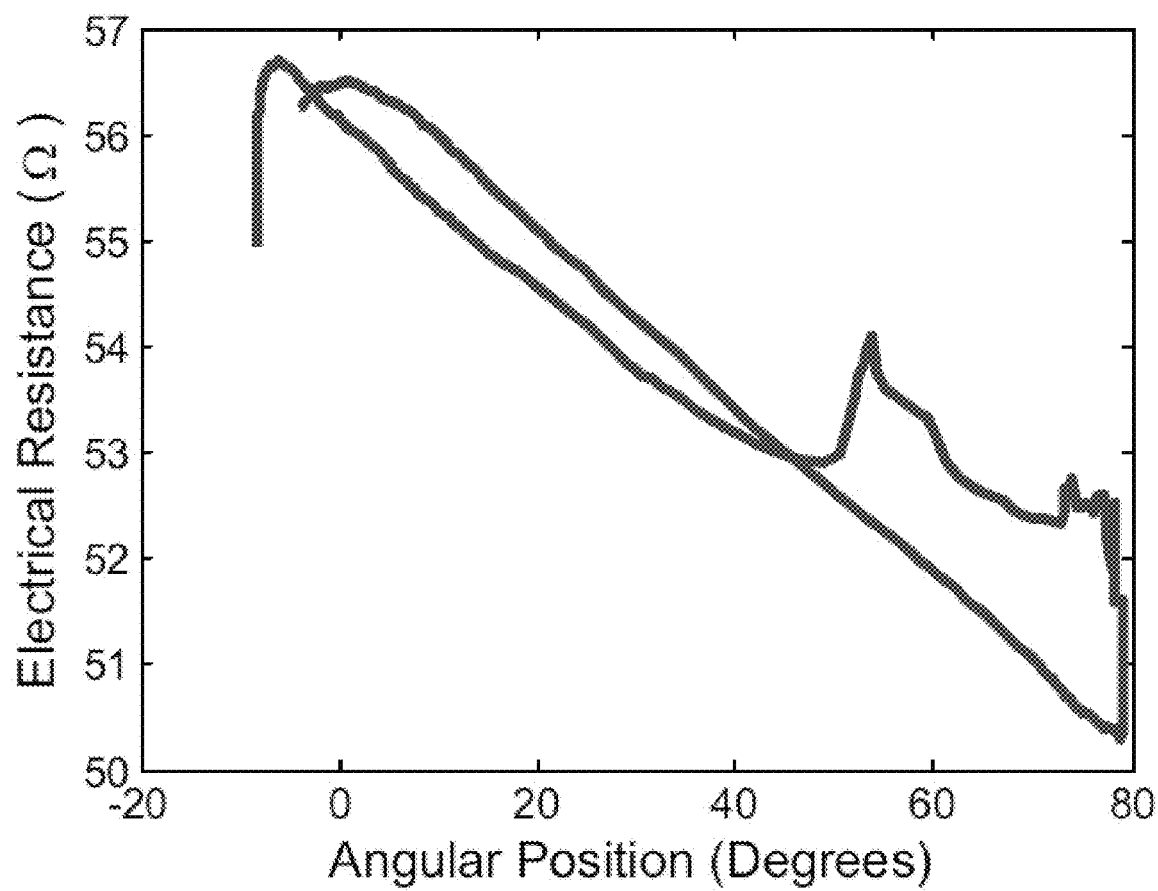
FIG. 11: Relationship between electrical resistance and angular position during open-loop experiment.

The experimental setup consisted of an SMA-actuated rotary manipulator, an Agilent E3631A controllable power supply, a dSPACE DS1104 board, and a central processing unit, the block diagram of which is shown FIG. 8. In this Example, a binary nickel-titanium alloy (nitinol) wire was used as an SMA actuator. A single degree-of-freedom bias-type manipulator used in this Example is shown in FIG. 9. In a bias-type manipulator, the upward force was generated by the SMA actuator, while the return force was generated by the bias spring. A 0.9-m nitinol wire was used to actuate the rotary manipulator. The nitinol wire was connected from the wire fixture, passing through the three pulleys on one side, then through the arm pulley, then through the three pulleys on the other side, and finally connected to the other wire fixture. Also, two different grooves were provided in lower pulleys; hence, the wires did not overlap. A list of parameters that describe the SMA-actuated rotary manipulator and their values is provided in Table 1 (FIG. 10). The actuation of SMA wire was controlled by adjusting the temperature through controlled joule heating by varying the electric current. The cooling took place through natural convection. The power supply was remotely controlled by a MATLAB program to apply a specific voltage. The amount of current passing through the SMA wire was also measured at that instant and was recorded. A position encoder was attached to the manipulator to measure the position of the manipulator arm. The position of the manipulator arm was measured, and the data were obtained in real time in MATLAB workspace through dSPACE DS1104 R&D board. The data of voltage and current were used to calculate the resistance of the wire, using ohms law. Thus, all the data were obtained in MATLAB workspace based on which further processing was done. FIG. 11 shows the relationship between electrical resistance and angular position during an open-loop experiment, where the voltage was increased linearly and then decreased in a similar fashion.

ANN Design

An ANN is a type of ML technique, which can be used to model a system based on data obtained from that system. ANN is an information processing system which is inspired from biological neural system's capability to learn from observation. A trained ANN can generalize any arbitrary input-output relationship. The two main components of an ANN are the neurons and the link between the neurons. The neuron acts as a processing element and is represented by a mathematical function called the activation function. These neurons are arranged in multiple layers, and this structure is commonly referred to as multilayer perceptron (MLP). The other important component of ANN is the link between the neurons. Each of these connections has a real valued parameter called weight associated with them. Once the training is complete, the values of weight vector are frozen, and the final weight vector encodes the input-output relationship. ANN has been used to model the hysteresis behavior of SMA. In this Example, the neural network toolbox of MATLAB was used to develop the ANN model. The inputs to ANN were electrical resistance of SMA, rate of change of current, and voltage applied. The output assigned to ANN was angular position of the rotary manipulator (in degrees). The Levenberg-Marquardt (LM) algorithm was used for training this ANN model. This algorithm is designed to approach second-order training speed without having to compute the Hessian matrix. The LM algorithm can be visualized as a combination of gradient descent algorithm and Newton's algorithm, thus having the advantages of both methods. The designing of ANN, method of weight initialization, and training was performed using known guidelines. The weight initialization was done using Nguyen-Widrow initialization algorithm. The hidden layer size was determined using network growing principle, whereas a single hidden layer was selected based on the universal approximation theorem. Early stopping mechanism was used to determine the number of epochs during training and to avoid over-fitting. Using the above techniques, the final design of ANN was obtained as 3 input layer neurons, 21 hidden layer neurons, and 1 output layer neurons.

Control Design

The control of SMA-actuated rotary manipulator was done using a modified variable structure control (VSC) algorithm. This algorithm was modified to include an integrator term. The logic of variable structure control-proportional-integral (VSC-PI) algorithm is given as follows:

$$u = \begin{cases} V_{high} & \text{if } \frac{s}{\phi} > 1 \\ V_{low} & \text{if } \frac{s}{\phi} < -1 \\ K_p\left(\frac{s}{\phi}\right) + K_i\left(\frac{s}{\phi}\right)dt & \text{if } 1 \geq \frac{s}{\phi} \geq -1 \end{cases}$$

where the boundary layer, $K_p$ is the controller proportional gain, $K_i$ is the integral gain, and s is defined as follows:

$$s = \left(\frac{d}{dt}(\theta_d - \theta)\right) + \lambda(\theta_d - \theta)$$

where θ is the angular position of the manipulator predicted by ANN, $\theta_d$ is the desired angular position of the manipulator, and 1 is the slope of sliding surface in phase plane which is determined experimentally. A boundary layer is the region around the switching surface s=0, where a different control law (PI control law in this case) applies, thereby resulting in smoother control. The thickness of boundary layer is the region where this control law applies. The values of all the above control parameters were obtained experimentally. An SMA actuator has a very slow actuation speed. The VSC algorithm, described above, provides fast actuation, especially when the manipulator arm is away from the desired point, compared to conventional linear algorithms. The other advantages of VSC algorithm in actuating SMA-actuated rotary manipulator include robust control and insensitivity to unmodeled system dynamics. This algorithm was implemented using a MATLAB program.

Effect on Ambient Temperature

Figure 12:
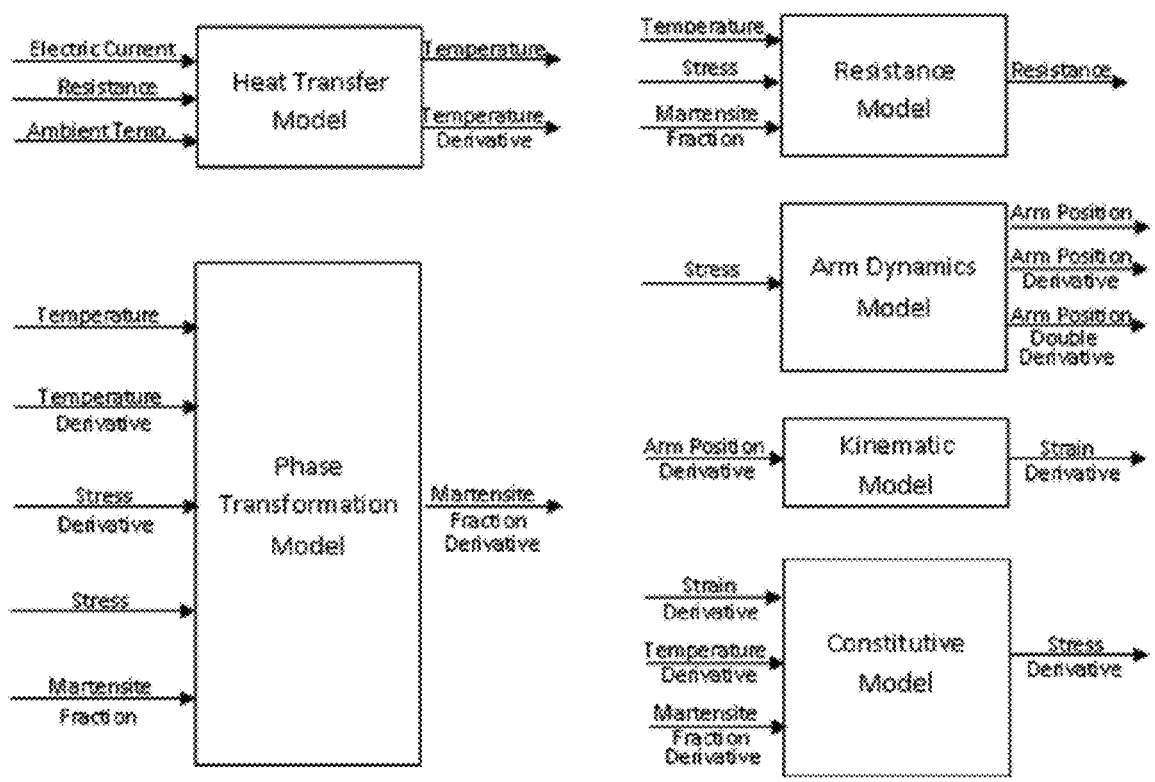
FIG. 12: Submodels that are combined to simulate the functionality of 1-DOF rotary manipulator. The input for the combined manipulator model is input voltage and ambient temperature while the output of the model is the manipulator position.

The effect of environmental temperature on SMA actuation and control is significant partly because resistance of the material is affected by the temperature. Moreover, in a bias-type actuator, the cooling of nitinol occurs by convection. Hence, it becomes important to analyze the performance of ANN when the environmental temperature is varied. To do this, an approximate phenomenological model was used to simulate the working of SMA-actuated rotary manipulator. The model used contains a number of submodels as shown in FIG. 12, and was implemented in MATLAB-Simulink environment. Signals were differentiated or integrated using the Simulink function as per the requirement. For training the ANN model, the Simulink model was simulated under varying ambient temperature conditions and open-loop position control. The values of resistance, rate of change of electric current, voltage applied, and manipulator angular position were recorded at each time step. These data were processed, and the ANN was trained by a method described below. The ANN was then tested with data from the same Simulink model when simulated under different ambient temperature conditions. The performance of ANN was evaluated based on its ability to predict the angular position under varying ambient temperature conditions. The results are described in the following section.

Results

ANN Training

Figure 13:
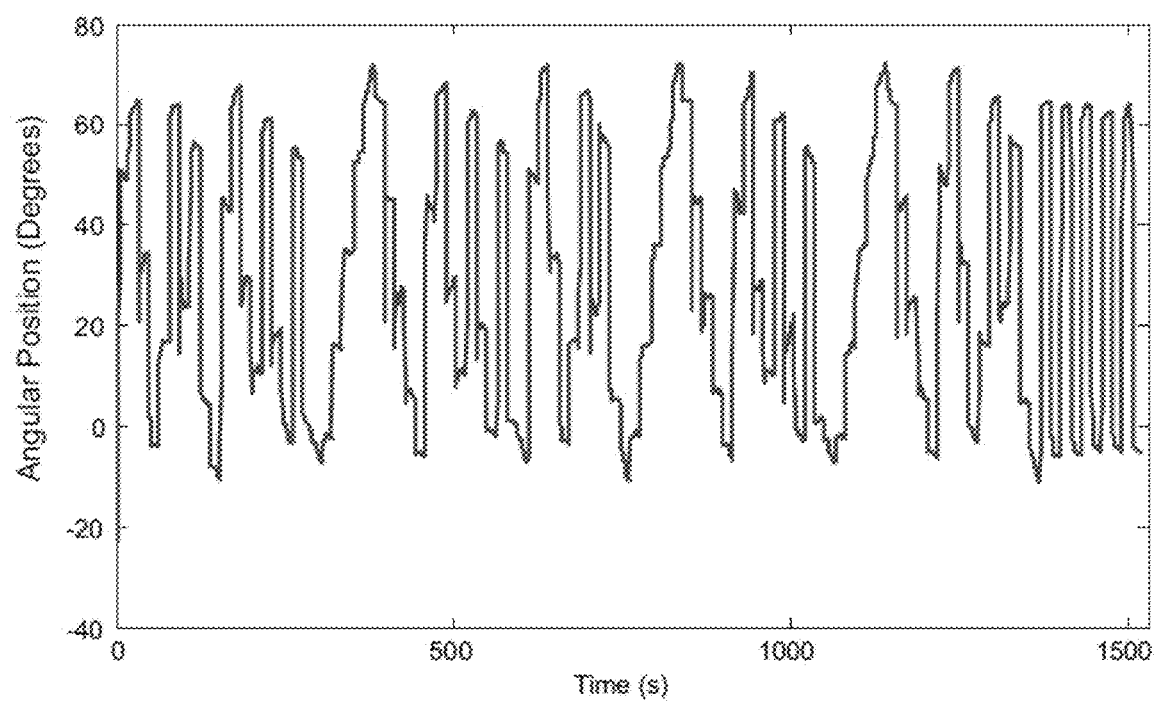
FIG. 13: Complex data used to train the artificial neural network (ANN) as described in the Examples.

This analysis was started by developing a robust ANN design which was able to accurately relate the electrical properties of SMA actuator and the manipulator angular position. The ANN was tested in complex situations. The SMA-actuated rotary manipulator was controlled using VSC-PI algorithm with position feedback from encoder, and the manipulator was made to track a complex signal. The position data collected from this experiment are shown in FIG. 13. These data were then used to train the ANN. The training was repeated a number of times to escape the problem of local minima associated with gradient-based approaches, and the model giving best performance is selected for further experiments.

ANN Testing

Figure 14:
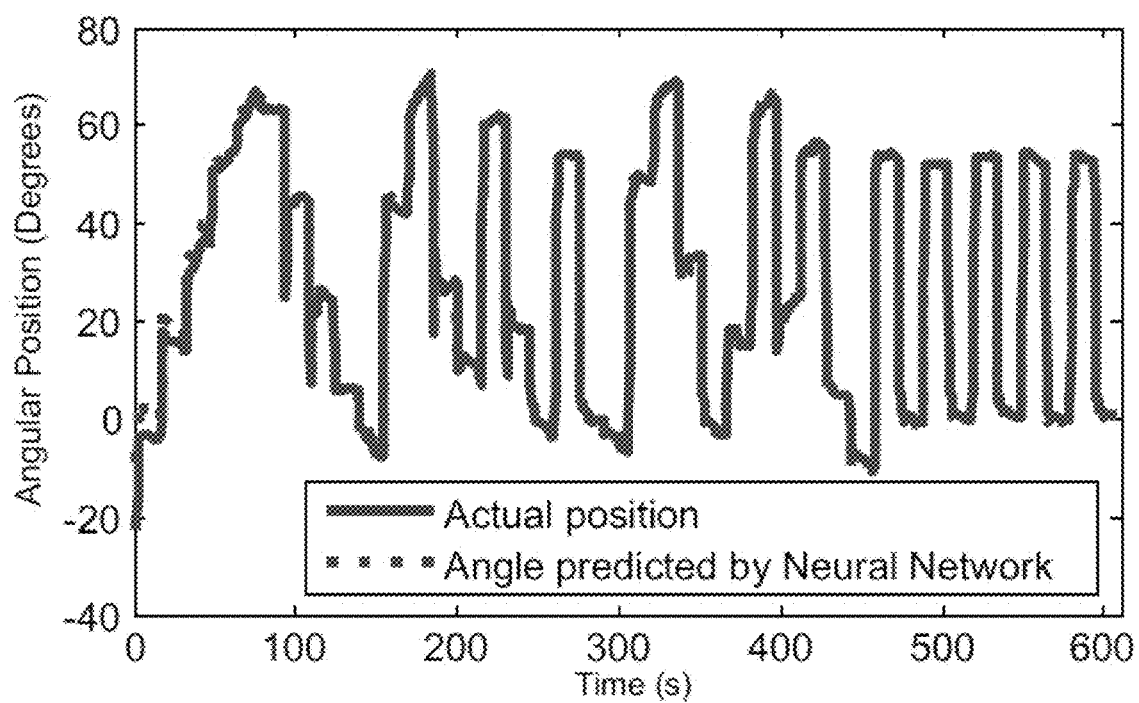
FIG. 14: Comparison of actual manipulator position and position predicted by ANN.
Figure 15A:
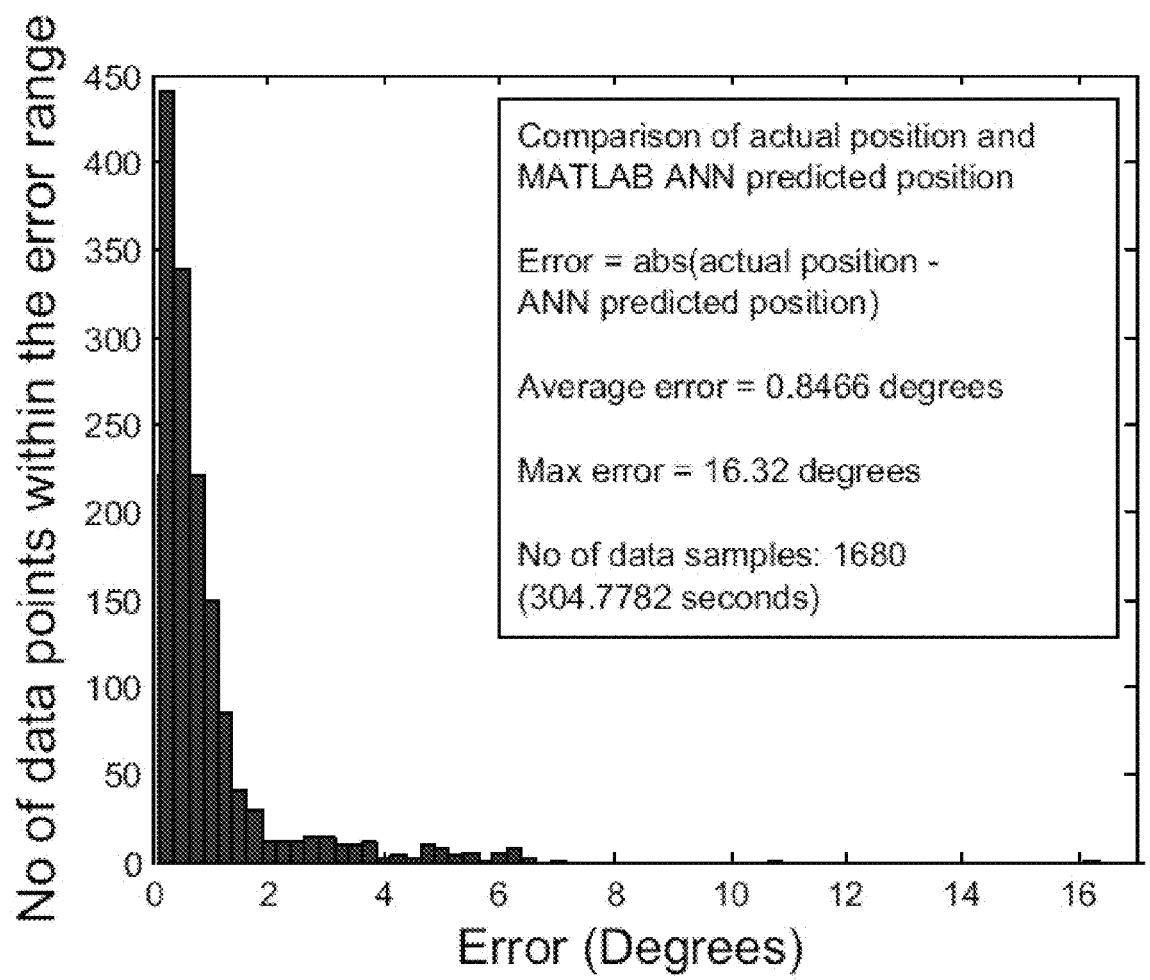
FIGS. 15A-15C: Histogram of difference between actual and ANN-predicted angular positions using MATLAB-trained ANN (FIG. 15A), histogram of difference between actual and ANN-predicted positions during control experiment (FIG. 15B), and histogram of difference between desired and actual positions during control experiment (FIG. 15C).

A similar experiment as described in the training section was performed, and the data from this experiment were used to test the developed ANN. The results of this testing are shown in FIG. 14. The analysis of error, that is, difference between actual and predicted positions, is presented as histogram, as shown in FIG. 15A. From the results, it is observed that the ANN is able to produce a good average accuracy of close to 0.8°.

Control System

Figure 16:
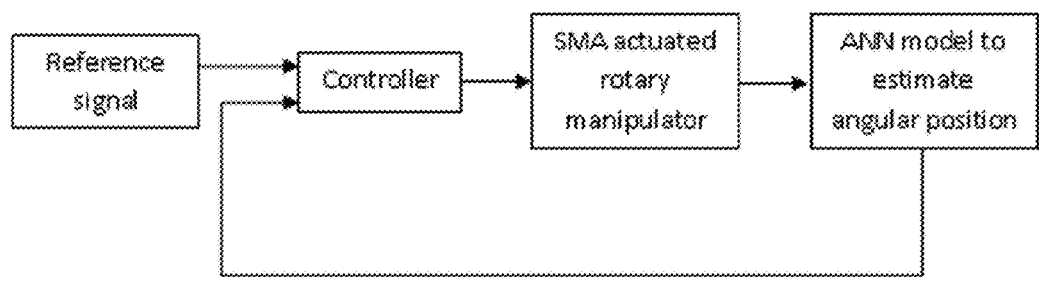
FIG. 16: Block diagram showing the working principle of position sensor-less control of SMA-actuated rotary manipulator using ANN-predicted position.

Then, the developed ANN was used to provide position feedback in a control scenario as described in the block diagram shown in FIG. 16. The effect of control parameters $\phi$ and $K_i$ was found to be significant. The use of nonzero $K_i$ helped in reducing the steady-state error. A sufficiently large value of $\phi$ was needed to provide stable operation as the ANN output had small fluctuation.

Experiments

Figure 15B:
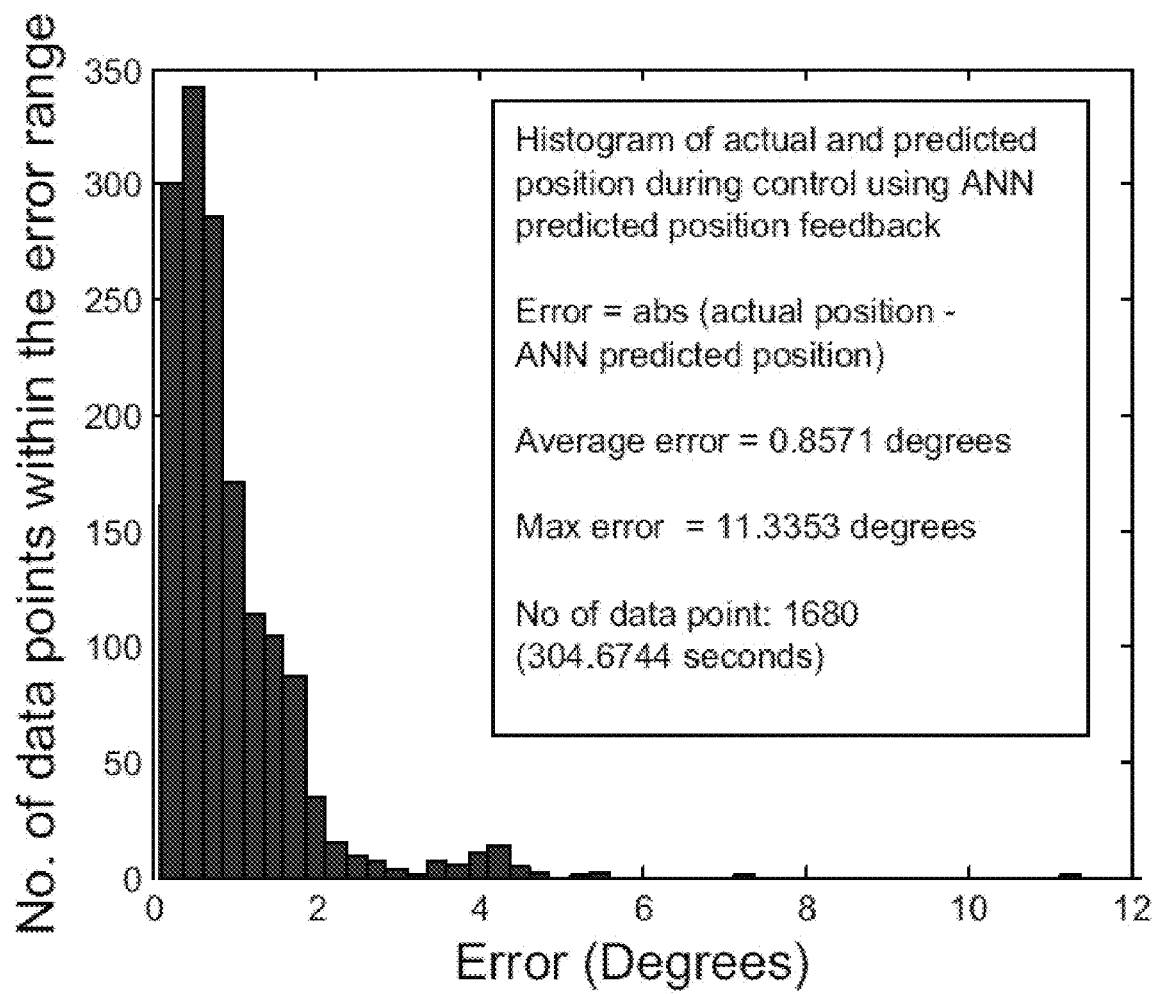
Figure 15C:
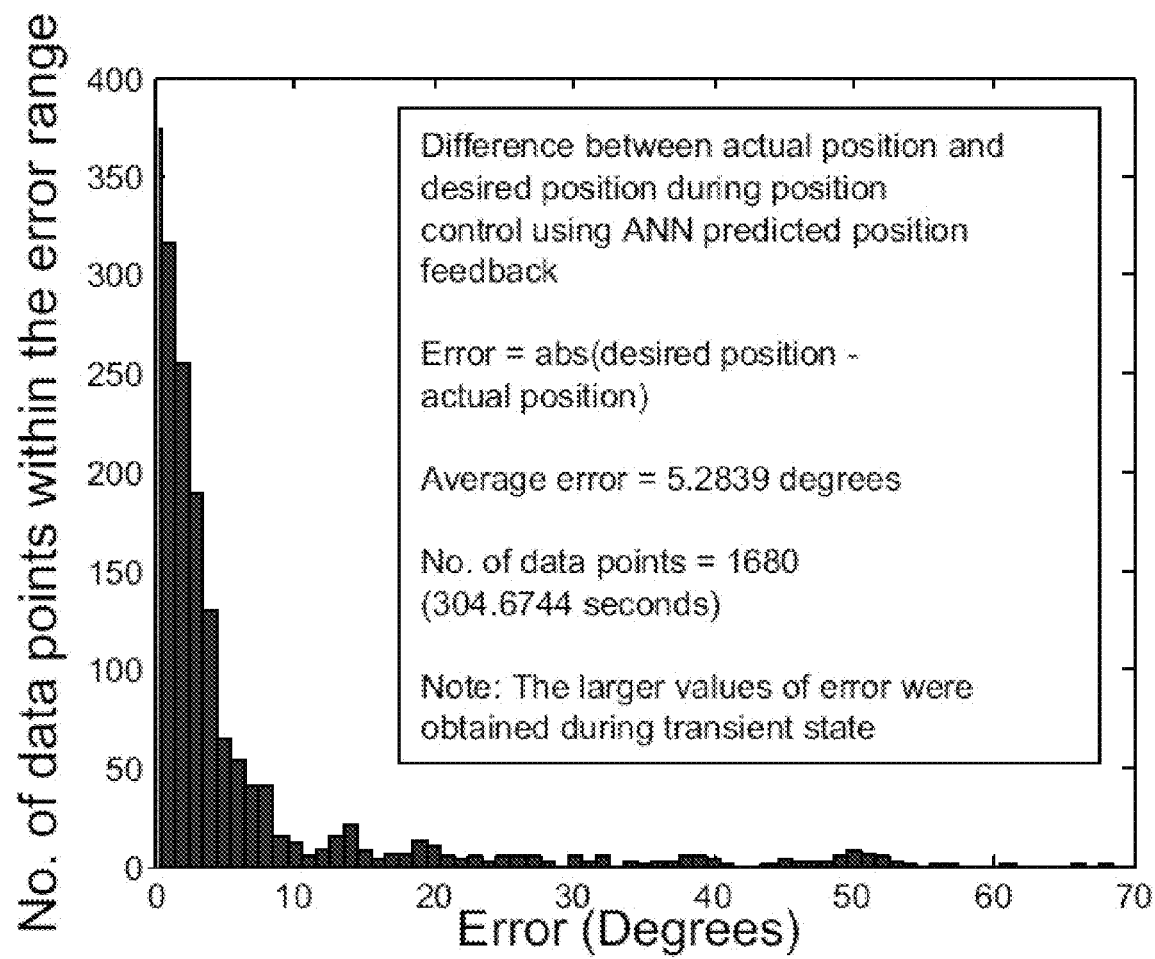
Figure 17:
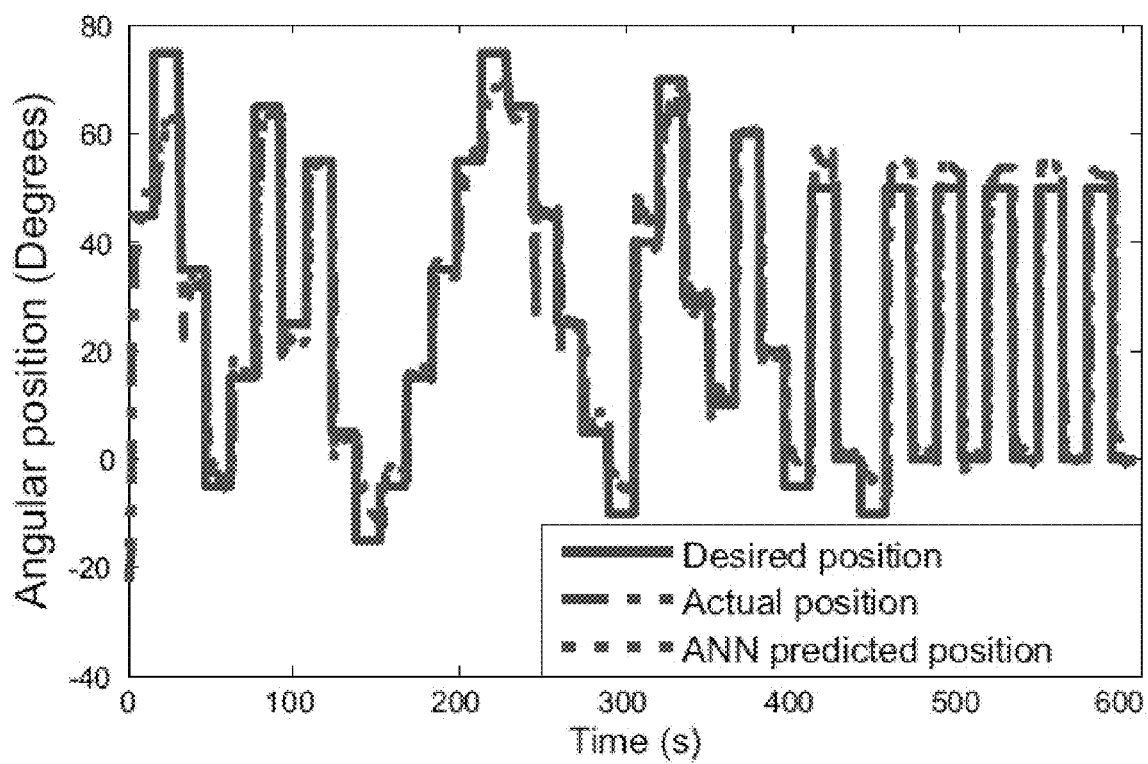
FIG. 17: Comparison of desired, actual, and ANN-predicted positions during control experiment.
Figure 18:
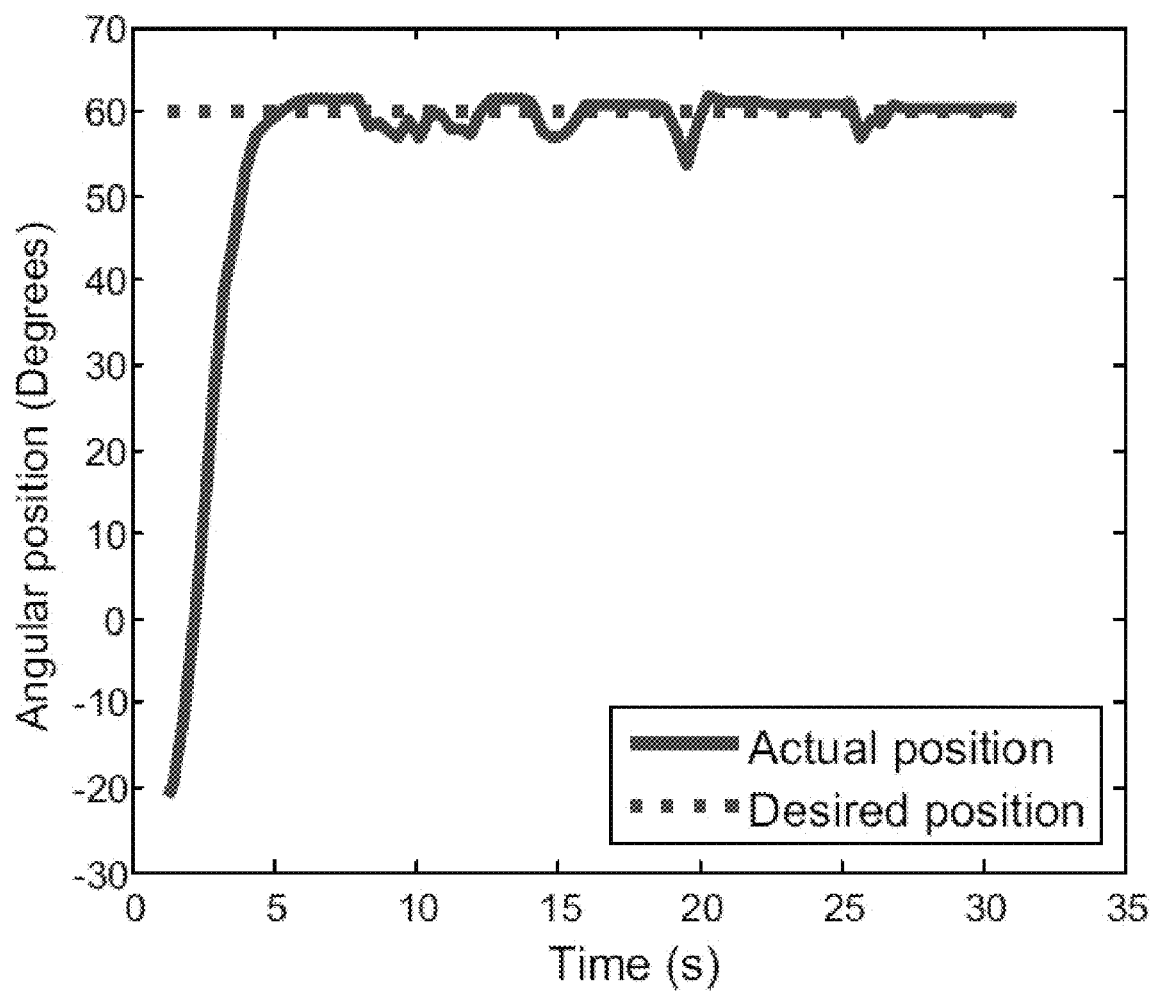
FIG. 18: Effect of mechanical disturbance, induced by manually tapping the rotary manipulator.
Figure 19:
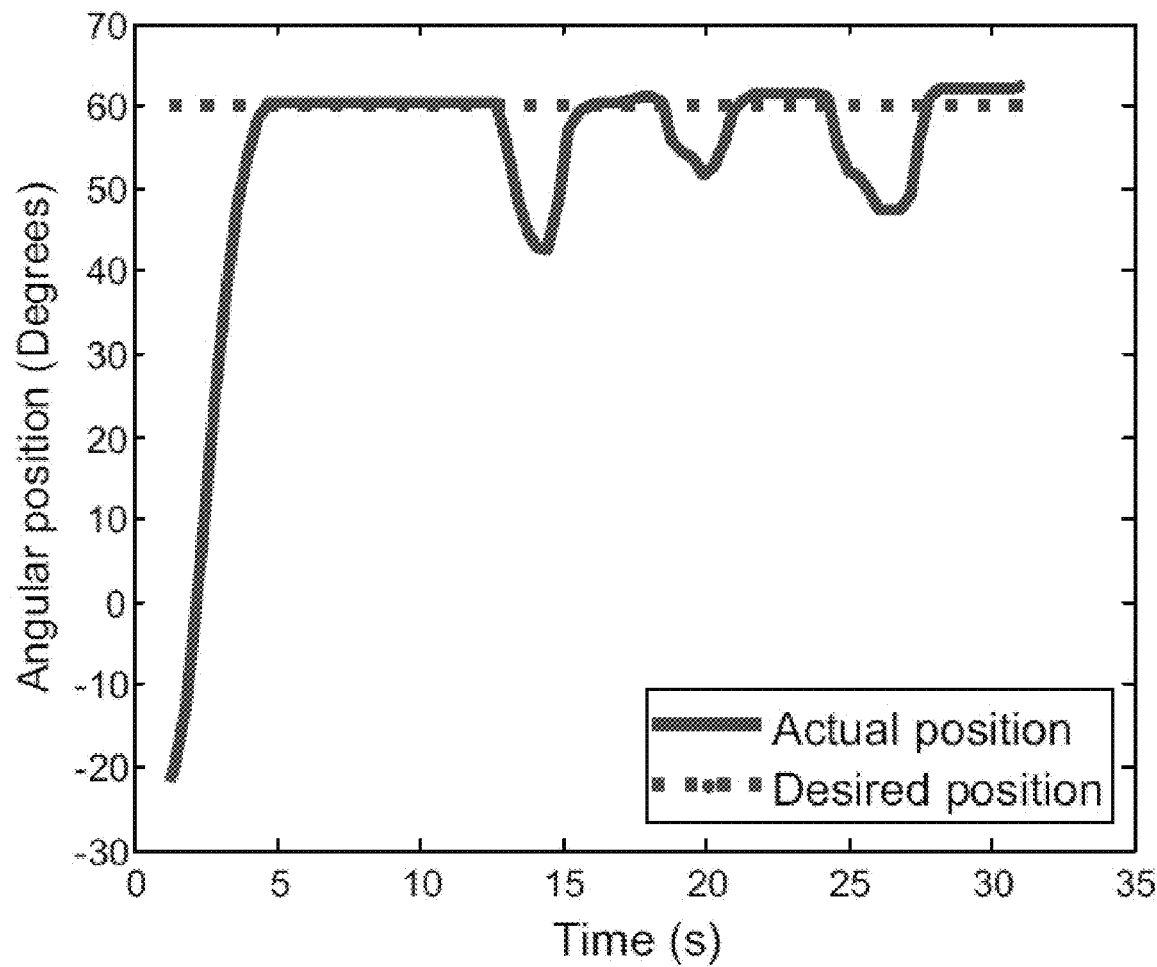
FIG. 19: Effect of thermal disturbance, induced by manually blowing air onto the SMA actuator.

Then, the control system using ANN-predicted position feedback was tested under different conditions. First, the system was tested by making it to track a complex signal. The result of these experiments, with a comparison of desired, actual, and predicted positions, is shown in FIG. 17. The ANN prediction error analysis, that is, difference between actual and predicted positions, is shown in a form of histogram in FIG. 15B. The control error analysis, that is, difference between actual and desired positions, is shown as a histogram in FIG. 15C. From the results, it is observed that the prediction error accuracy was close to 0.8°, and the control error accuracy was close to 5°, which is good considering no external sensors are used. The system was also made to track simpler signals such as square wave, multi-step input, and staircase signal. An average control accuracy of 2°-3° was obtained in these experiments. The control system was also tested by subjecting it to thermal and mechanical disturbances. The thermal disturbance was introduced by blowing air onto the system when the system was tracking a particular angular position. This cooled the SMA wires at a faster rate, and thus, the error was observed. Similarly, the mechanical disturbance was introduced by manually tapping the rotary arm when the system was tracking an angular position. This caused the arm to move down further, thereby introducing error in the system. However, as soon as the disturbances were removed, the system returned to the desired position. Thus, it was found that the system was able to reject these small disturbances, even though the ANN was not trained in these scenarios, as shown in FIGS. 18-19.

Effect of Ambient Temperature

Figure 20:
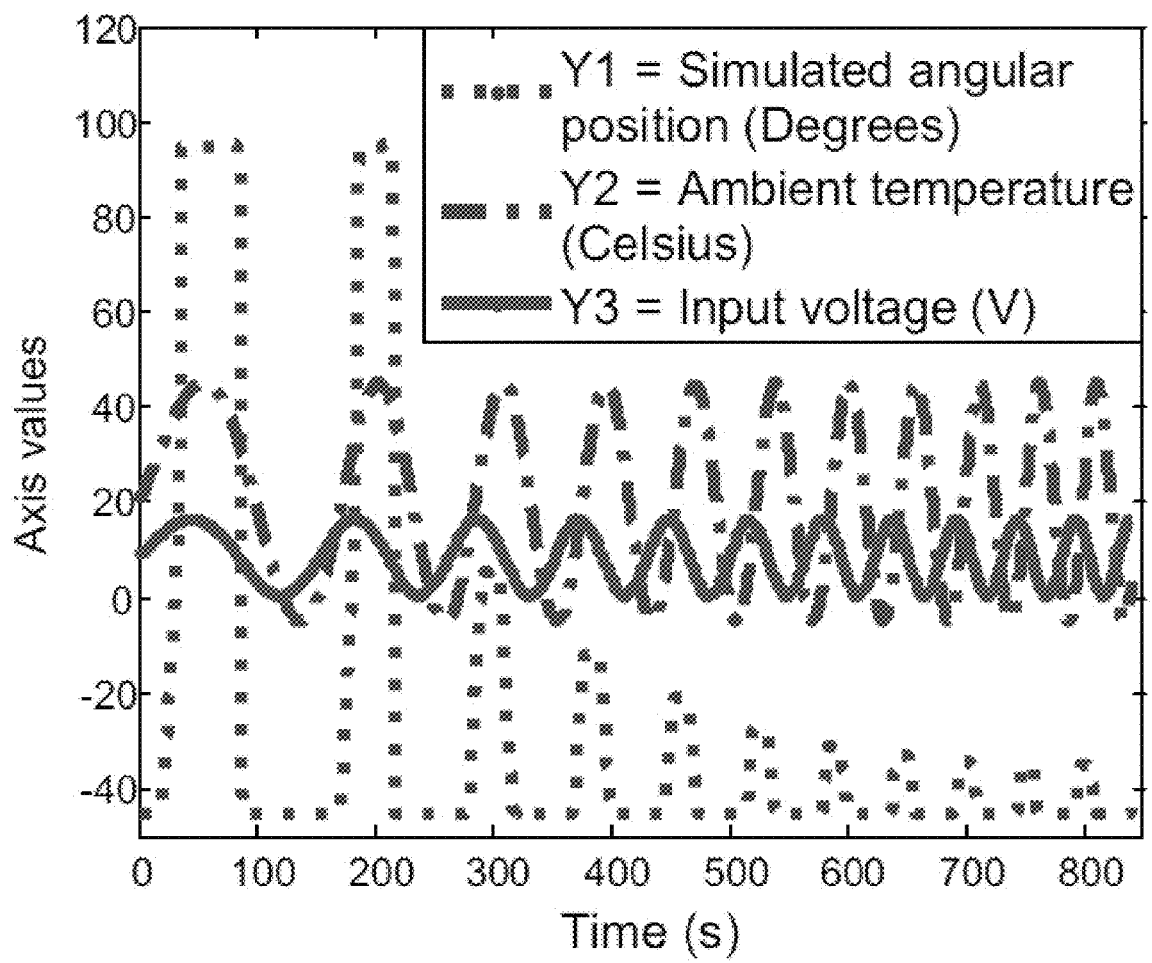
FIG. 20: Variation of input voltage, ambient temperature, and simulated manipulator angle when collecting data for ANN training.
Figure 21:
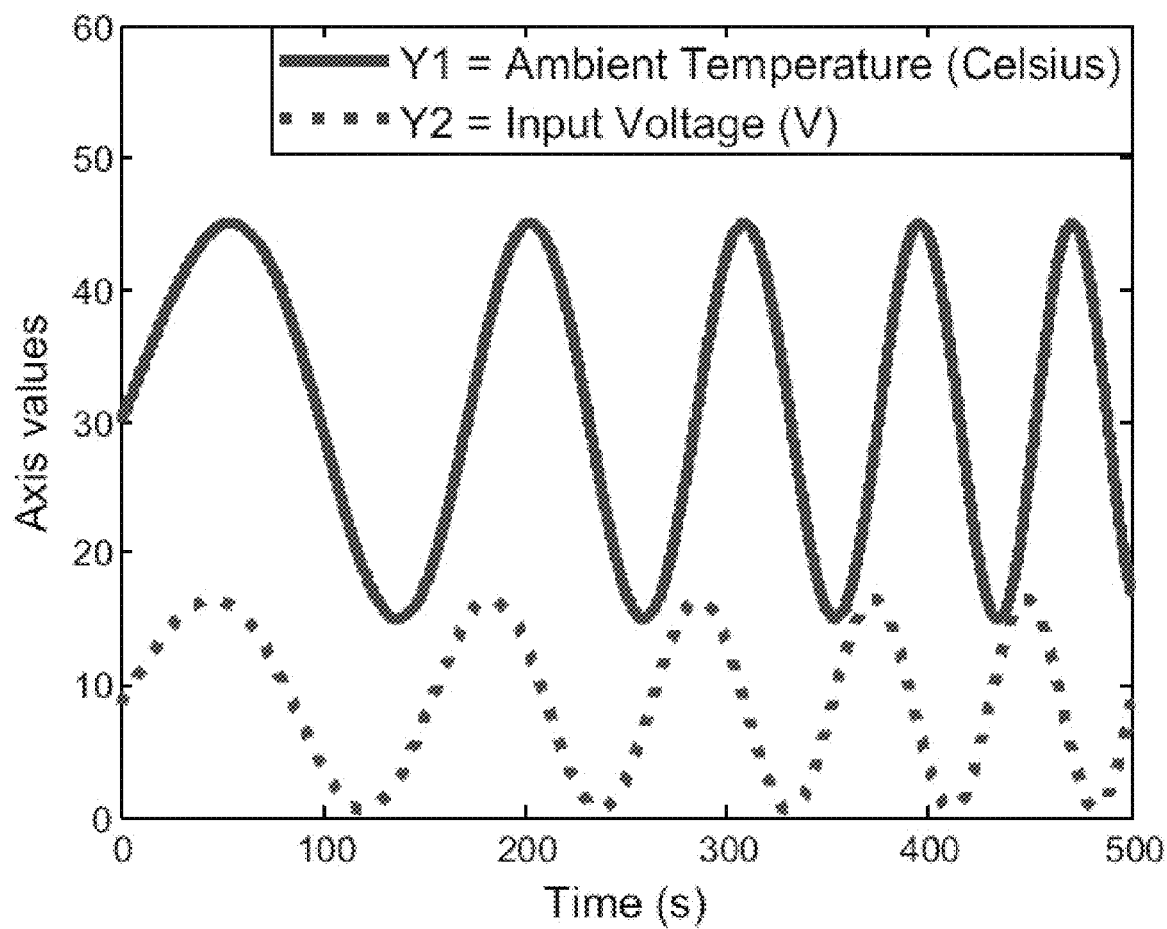
FIG. 21: Variation of ambient temperature and input voltage when simulating in the first scenario.
Figure 22:
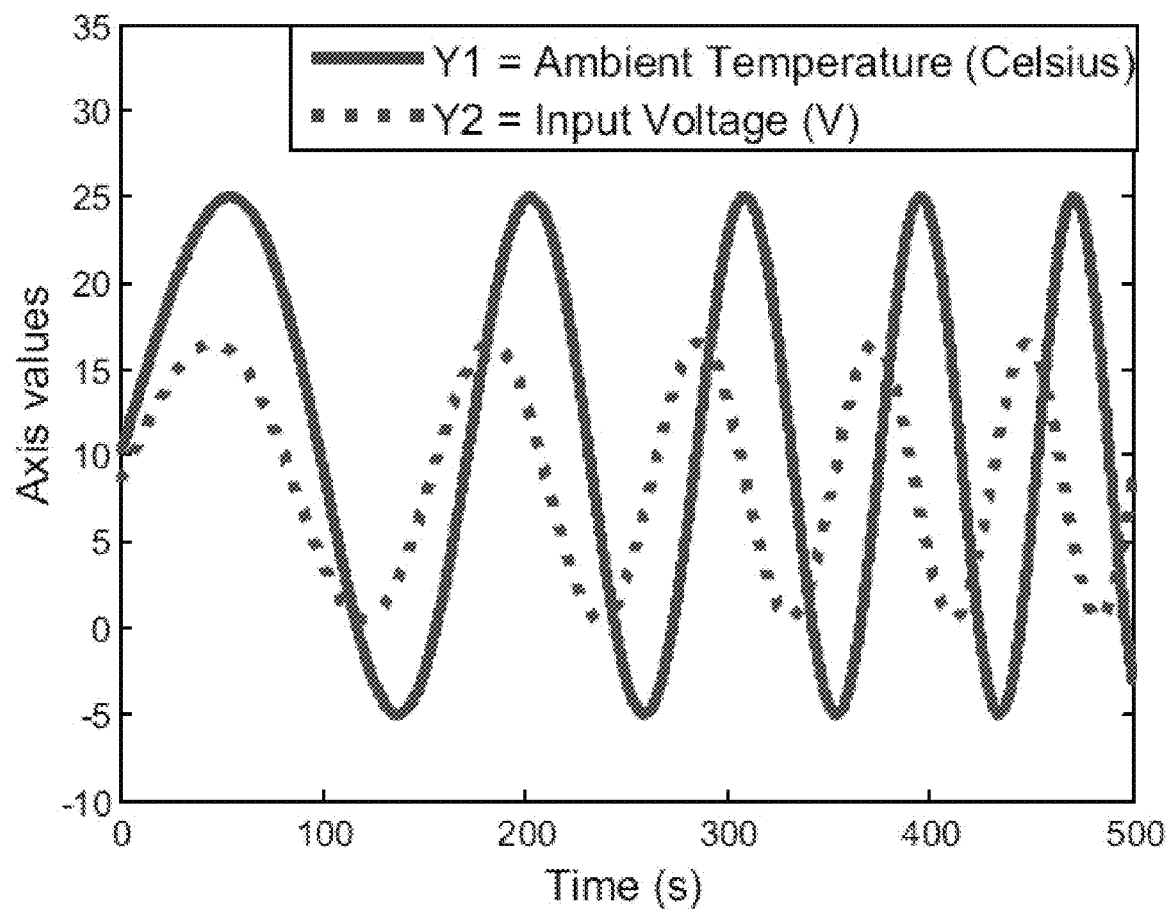
FIG. 22: Variation of ambient temperature and input voltage when simulating in the second scenario.
Figure 23:
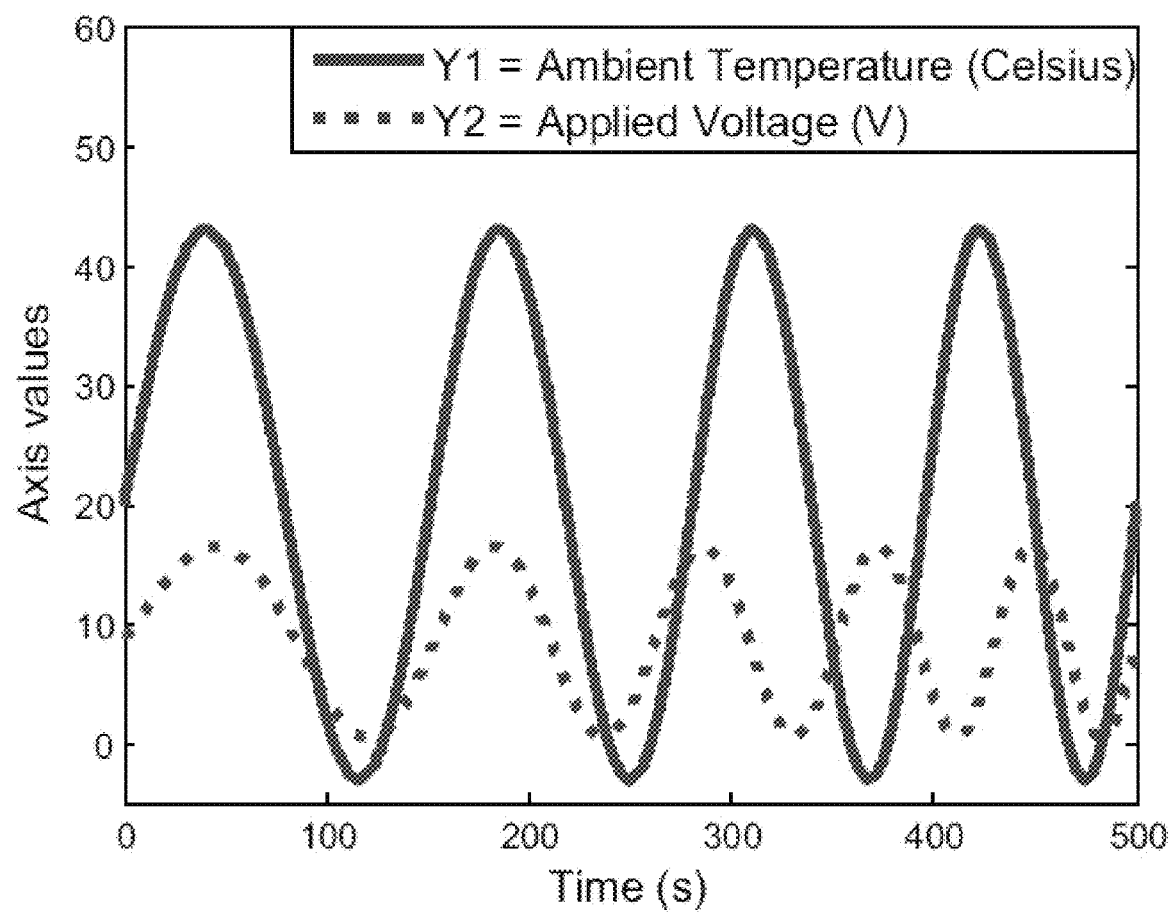
FIG. 23: Variation of ambient temperature and input voltage when simulating in the third scenario.
Figure 24:
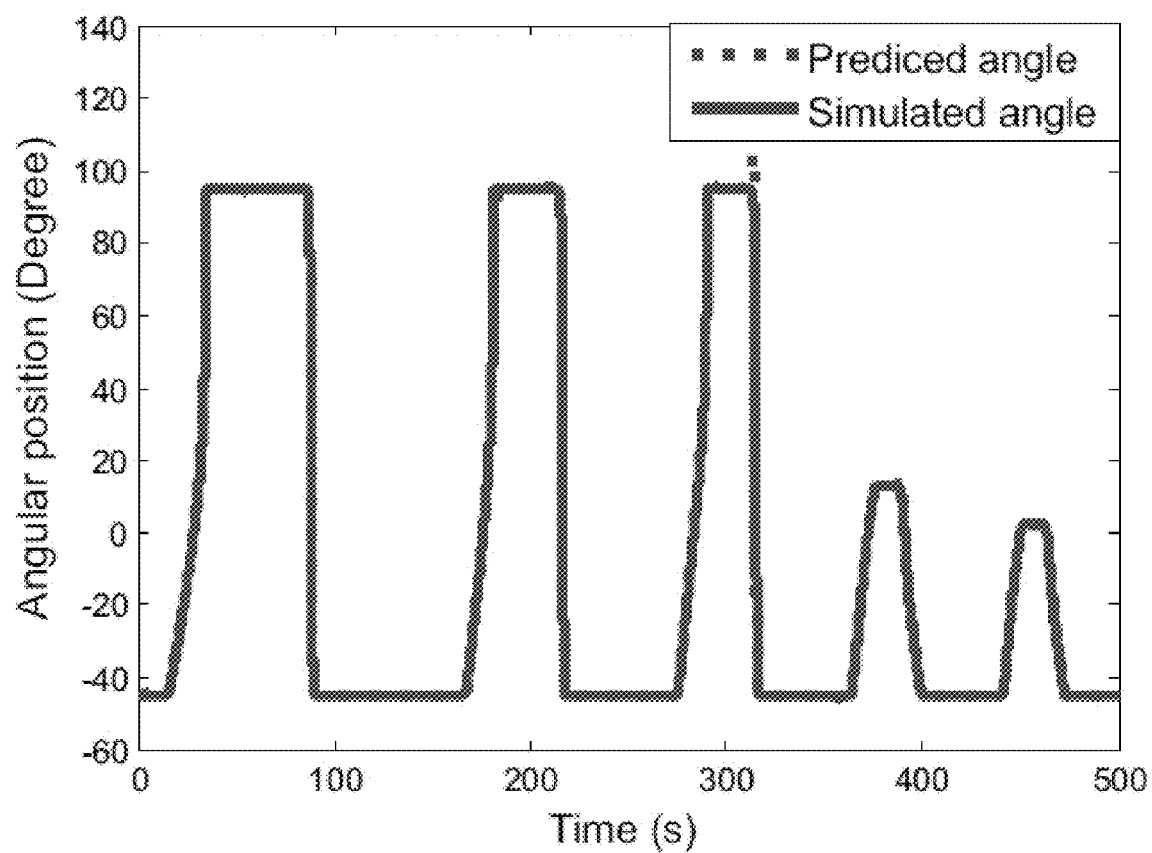
FIG. 24: Comparison of simulated angle and ANN-predicted angle in the first scenario.
Figure 25:
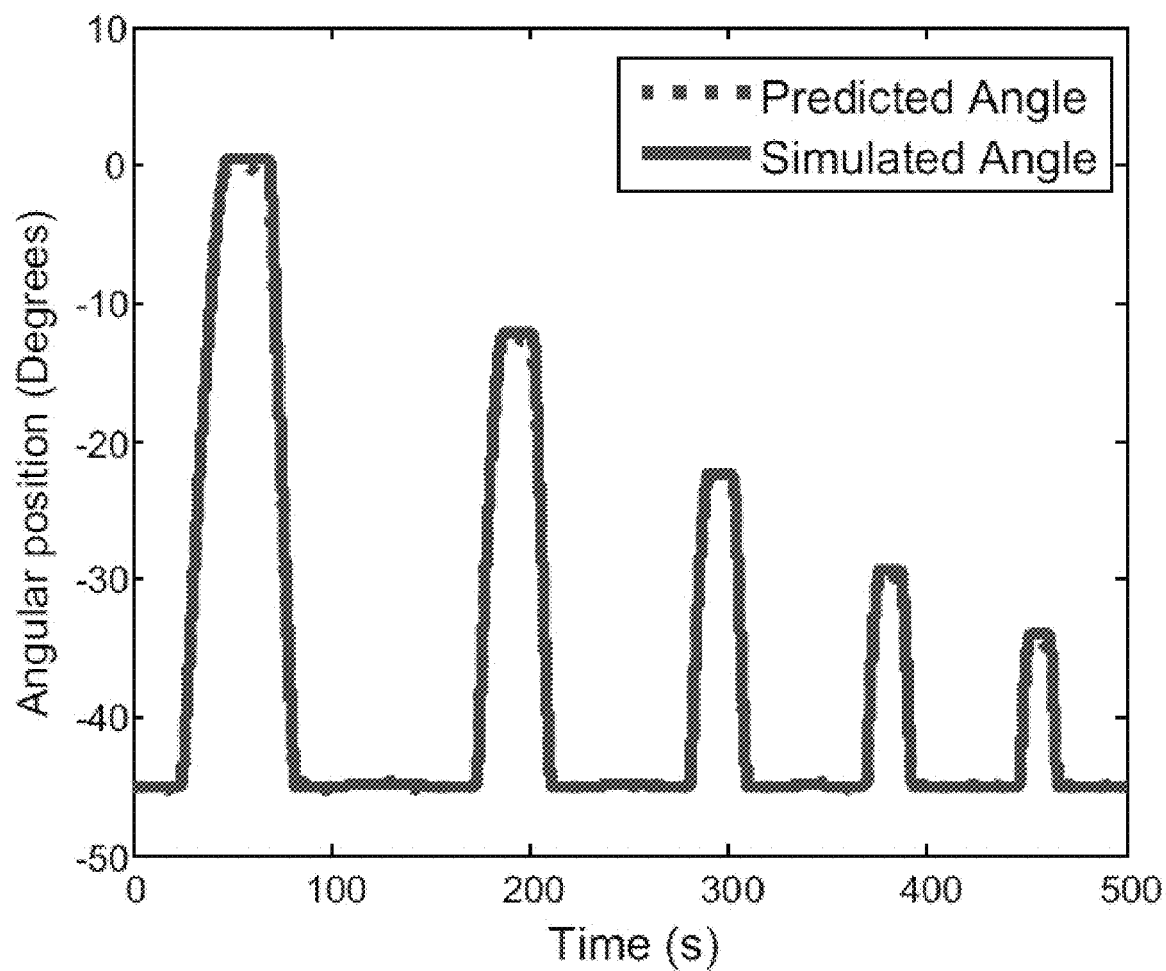
FIG. 25: Comparison of simulated angle and ANN-predicted angle in the second scenario.
Figure 26:
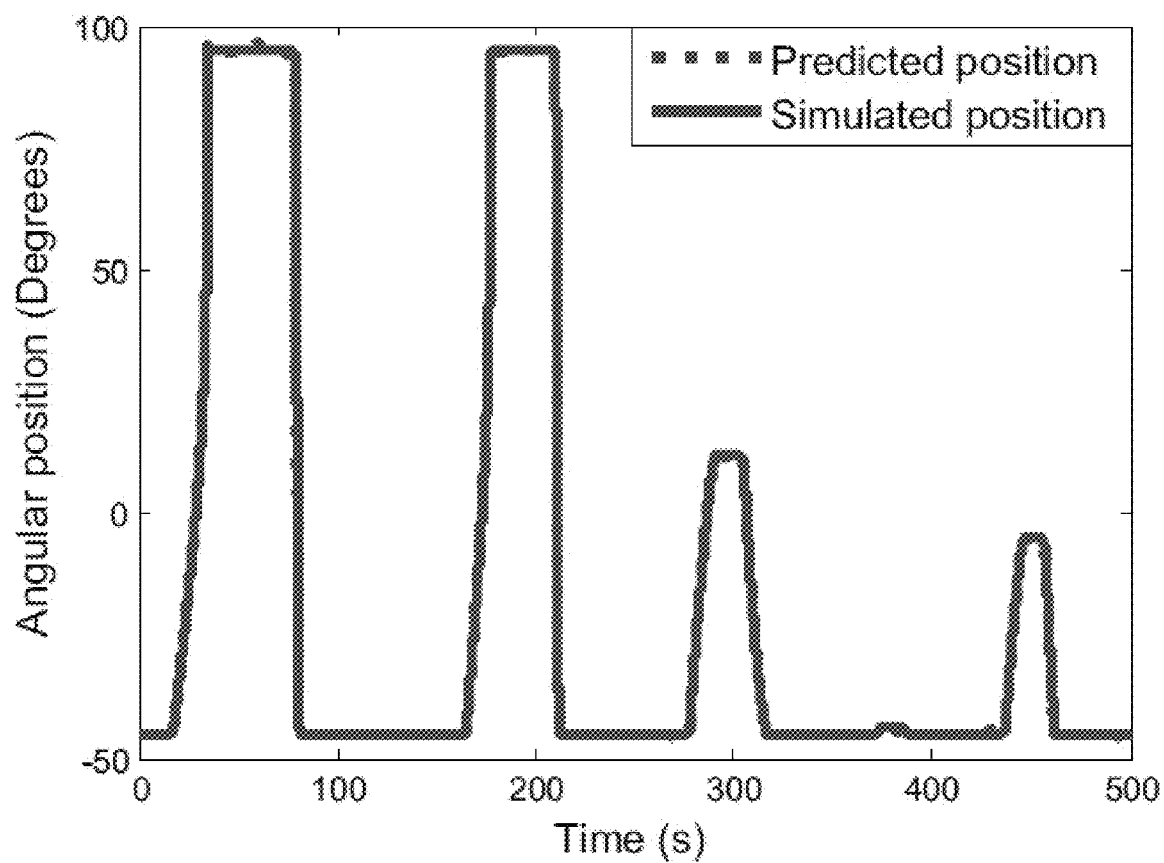
FIG. 26: Comparison of simulated angle and ANN-predicted angle in the third scenario.

The ANN was tested by varying the ambient temperatures. For this, ANN was developed from simulation as explained in section "Effect of ambient temperature." The simulation data were obtained using a chirp-sine input voltage (i.e. a sine wave with uniformly varying frequencies) with amplitude=8 V, bias=8.5 V, and angular frequency varying from 0.005 to 0.02 rad/s. At the same time, the ambient temperature was varied using a chirp-sine input voltage with amplitude=25V, bias=20V, and frequency from 0.004 to 0.02 rad/s. Thus, the simulation was performed with ambient temperature varying from 25° C. to 45° C. The simulation was performed for 750 s, and the recorded data were used for training an ANN. The values of applied voltage, ambient temperature, and simulated manipulator position are shown in FIG. 20. The ANN was then tested in three scenarios. First, the data were obtained by performing simulation at high ambient temperature range, that is, from 15° C. to 45° C. In the second simulation, the temperature range was varied from 25° C. to 15° C. In both the cases, the frequency variation was at the same rate as used in the training data. The variation of input voltage and ambient temperature during these two simulations is shown in FIGS. 21-22, respectively. In the third simulation, the temperature was varied from 23° C. to 43° C., and the angular frequency of the sine wave was varied from 0.006 to 0.01 rad/s, as shown in FIG. 23. The ANN test results for these three scenarios are shown in FIGS. 24-26, respectively. The average prediction error, that is, the difference between simulated angle and ANN-predicted angle, in these three test cases was 0.09°, 0.17°, and 0.15°, respectively. From the results, it is observed that the ANN is able to differentiate the ambient temperature variations if such data are included in training. In the first scenario, few data points with high prediction error are observed. This could be overcome by collecting more data point in those regions when training the ANN.

CONCLUSION

In this Example, a successful attempt has been made to develop a technique for sensorless position control of SMA-actuated rotary manipulator using ANN. First, an ANN was developed that can estimate the angular position using available electrical signals, so that the requirement of any external position sensors is eliminated. This ANN was then tested in different scenarios with varying complexities. The designed ANN was able to estimate the angular position accurately (average accuracy of 0.8°). The accuracy was good during both major and minor hysteresis loops, even though the complex thermomechanical relationship between stress and temperature altered the transformation temperature significantly at various instances of operation. The ANN was then used in VSC-PI control algorithm for sensorless control of SMA-actuated rotary manipulator. Multiple experiments were performed, where the rotary manipulator was made to track different reference signals of varying complexities. The SMA actuator was able to track the signals with an average accuracy of 5°. Also, as the SMAs have slow actuation speed, they had a larger response time. Since these values were also included in average error calculation, the value of steady-state error was concluded to be less than 5°. The system was also subjected to external disturbances and was found to be robust. The performance of ANN was not affected by the speed of actuation but was sensitive to large change in pre-stress and load on the manipulator. This is because the training data included scenarios with different speeds of actuation while only one prestress and load condition was used. Thus, by incorporating variation of pre-stress in training data, the model could be made more robust to load and pre-stress changes. Thus, it is concluded that the design can be implemented in any scenario where a small tolerance of error (around 5°) is acceptable. Then, the developed ANN was tested under varying ambient temperatures. For this, a simulation model was used to generate data, and an ANN was trained. The ANN was then tested in three scenarios, and accurate prediction results were obtained in all the three cases. The ANN was able to operate with good accuracy under the test condition of varying ambient temperature ranges of 25° C. to 45° C. with varying frequencies. Thus, it is concluded that the ANN is robust to ambient temperature changes if trained with proper data.

Certain embodiments of the devices, systems, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. An organ repositioner device comprising:
an inflatable balloon mounted on a bendable tube defining a lumen, the lumen housing an assembly of a shape memory (SM) element and a superelastic (SE) element, wherein the SM element comprises a first shape memory alloy and has a first shape set form, and the SE element comprises a second shape memory alloy and has a second shape set form;
wherein the bendable lumen bends upon shape transformations of the assembly, and the assembly has an equilibrium shape between the first shape set form and the second shape set form.

2. The organ repositioner device of claim 1, wherein upon cooling the organ repositioner device deforms toward the second shape set form, and heating drives the organ repositioner device toward the first shape set form.

3. The organ repositioner device of claim 1, wherein the SM element is a round wire and the SE element is a flat wire, wherein either the round wire is wrapped around the flat wire or the flat wire is wrapped around the round wire.

4. The organ repositioner device of claim 1, wherein the first shape memory alloy comprises a NiTi alloy.

5. The organ repositioner device of claim 1, wherein the second shape memory alloy comprises a NiTi alloy.

6. The organ repositioner device of claim 1, wherein the first shape memory alloy and the second shape memory alloy are different NiTi alloys.

7. The organ repositioner device of claim 1, further comprising a controller in electrical communication with the SM element and the SE element, wherein the controller is configured to apply a voltage in the organ repositioner device.

8. The organ repositioner device of claim 1, wherein the organ repositioner device comprises a plurality of inflatable balloons mounted on the bendable tube.

9. A method of administering a radiation therapy to a prostate, the method comprising:
using the organ repositioner device of claim 1 to displace a rectum away from a prostate with respect to a radiation beam path; and
administering a radiation therapy to the prostate through the radiation beam path.

10. The method of claim 9, wherein the organ repositioner device comprises a controller that monitors electrical resistance in the organ repositioner device to determine an actuation state of the organ repositioner device.

* * * * *